United States Patent
Schulz et al.

(10) Patent No.: US 6,306,555 B1
(45) Date of Patent: Oct. 23, 2001

(54) IODONIUM SALTS AS LATENT ACID DONORS

(75) Inventors: Reinhard Schulz, Staufen-Wettelbrunn (DE); Jean-Luc Birbaum, Binningen (CH); Jean-Pierre Wolf, Maisprach (CH); Stephan Ilg, Giebenach (CH); Hitoshi Yamato, Takarazuka; Toshikage Asakura, Minoo, both of (JP)

(73) Assignee: CIBA Specialty Chemicals Corp., Tarrytown, NY (US)

( * ) Notice: Subject to any disclaimer, the term of this patent is extended or adjusted under 35 U.S.C. 154(b) by 0 days.

(21) Appl. No.: 09/740,205

(22) Filed: Dec. 18, 2000

(30) Foreign Application Priority Data

Dec. 21, 1999 (CH) .................................................. 2343/99

(51) Int. Cl.$^7$ ..................................................... G03F 7/004
(52) U.S. Cl. ........................ 430/270.1; 430/914; 522/31; 556/64; 568/1; 568/6; 568/16; 568/28
(58) Field of Search ........................... 522/31; 430/270.1, 430/914; 556/64; 568/1, 6, 16, 28

(56) References Cited

U.S. PATENT DOCUMENTS 6,235,807   5/2001   Misev ..................................... 522/15

FOREIGN PATENT DOCUMENTS

98/46647   10/1998   (WO) .

OTHER PUBLICATIONS

Chemical Abstracts 127:292975.*
J. Crivello, UV Curing: Science and Technology, "Photoinitiated Cationic Polymerization", (1980), pp. 24–77.
J. Crivello et al., Macromolecules, vol. 10, No. 6, (1977) pp. 1307–1315.
J. Crivello, Ann. Rev. Mater. Sci., (1983), vol. 13, pp. 173–190.
J. Crivello, Journal of Polymer Science, Part A: Polymer Chemistry, vol. 37, pp. 4241–4254, (1999).
A. Shah et al., J. Chem. Soc. Perkin Trans 1, (1997), pp. 2463–2465.

* cited by examiner

Primary Examiner—Rosemary Ashton
(74) Attorney, Agent, or Firm—Tyler A. Stevenson

(57) ABSTRACT

Radiation-sensitive compositions comprising
(a1) a cationically or acid-catalytically polymerisable or crosslinkable compound or
(a2) a compound that increases its solubility in a developer under the action of acid; and
(b) at least one diaryliodonium salt of formula I

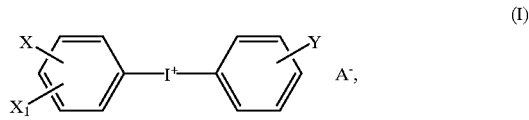

$X$ is branched $C_3$–$C_{20}$alkyl or $C_3$–$C_8$cycloalkyl;
$X_1$ is hydrogen, linear $C_1$–$C_{20}$alkyl, branched $C_3$–$C_{20}$alkyl or $C_3$–$C_8$cycloalkyl; with the proviso that the sum of the carbon atoms in X and $X_1$ is at least 4;
Y is linear $C_1$–$C_{10}$alkyl, branched $C_3$–$C_{10}$alkyl or $C_3$–$C_8$cycloalkyl;
$A^-$ is a non-nucleophilic anion, selected from the group $(BF_4)^-$, $(SbF_6)^-$, $(PF_6)^-$, $(B(C_6F_5))_4^-$, $C_1$–$C_{20}$alkylsulfonate, $C_2$–$C_{20}$haloalkylsulfonate, unsubstituted $C_6$–$C_{10}$arylsulfonate, camphorsulfonate, and $C_6$–$C_{10}$arylsulfonate substituted by halogen, $NO_2$, $C_1$–$C_{12}$alkyl, $C_1$–$C_{12}$halo-alkyl, $C_1$–$C_{12}$alkoxy or by $COOR_1$; and
$R_1$ is $C_1$–$C_{20}$alkyl, phenyl, benzyl; or phenyl mono- or poly-substituted by $C_1$–$C_{12}$alkyl, $C_1$–$C_{12}$alkoxy or by halogen;
with the proviso that the two phenyl rings on the iodine atom are not identically substituted.

18 Claims, No Drawings

IODONIUM SALTS AS LATENT ACID DONORS

The invention relates to selected iodonium salt compounds and to their use as photoinitiators.

It is known to use iodonium salts as photoinitiators in cationically polymerisable compositions. Such disclosures can be found, for example, in J. V. Crivello, "Photoinitiated Cationic Polymerization" in: UV Curing: Science and Technology, Editor S. P. Pappas, pages 24–77, Technology Marketing Corporation, Norwalk, Conn. 1980, ISBN No. 0-686-23773-0; J. V. Crivello, J. H. W. Lam, Macromolecules, 10, 1307 (1977) and J. V. Crivello, Ann. Rev. Mater. Sci. 1983, 13, pages 173–190 and J. V. Crivello, Journal of Polymer Science, Part A: Polymer Chemistry, Vol. 37, 4241–4254 (1999). WO 98/46647 discloses 4,4'-dialkylphenyliodonium compounds containing at least one isopropyl group in photocurable compositions. J. Chem. Soc. Perkin Trans. 1, 1997,17, pages 2463–2465 discloses a special process for the manufacture of asymmetrically substituted diaryliodonium triflates and trifluoroacetates, which can be used to prepare 4-tert-butylphenyl-2'-methylphenyliodonium triflate and trifluoroacetate, respectively.

The hitherto known iodonium-salt-containing radiation-reactive compositions available for technical uses have a number of disadvantages that are attributable to the iodonium salts used. For example, diphenyliodonium salts have poor solubility in the formulations, which limits their use in practice since only a low concentration of the iodonium salt can be used, otherwise there is a risk that it will crystallise out. Moreover, phenyliodonium salts release benzene as a photoproduct, which can migrate out of the cured compound or coating (e.g. printing ink) into the substrate or is released into the environment and is highly undesirable for toxicological reasons (e.g. in the printing of foodstuffs packaging). Whilst the substitution of one of the phenyl rings by longer-chained alkyl or alkoxy substituents can improve the solubility, the disadvantage of the formation of benzene remains. Large substituents generally not only reduce the reactivity, but also make it significantly more difficult to handle the compounds, which are then no longer obtained in crystalline form and can be prepared only with difficulty in the high purity that is required especially for use in the field of microelectronics. It has also been shown that phenylaryliodonium salts, from which benzene may be produced upon exposure, give a positive reaction in the AMES test, which is used for initial detection of mutagenic potential, that is to say they are suspected of having mutagenic activity.

It has now been found that radiation-sensitive compositions comprising
(a1) a cationically or acid-catalytically polymerisable or crosslinkable compound, or
(a2) a compound that increases its solubility in a developer under the action of acid; and
(b) at least one diaryliodonium salt of formula I

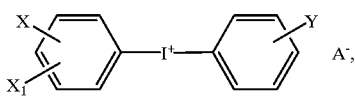

(I)

wherein
X is branched $C_3$–$C_{20}$alkyl or $C_3$–$C_8$cycloalkyl;
$X_1$ is hydrogen, linear $C_1$–$C_{20}$alkyl, branched $C_3$–$C_{20}$alkyl or $C_3$–$C_8$cycloalkyl; with the proviso that the sum of the carbon atoms in X and $X_1$ is at least 4;
Y is linear $C_1$–$C_{10}$alkyl, branched $C_3$–$C_{10}$alkyl or $C_3$–$C_8$cycloalkyl;
$A^-$ is a non-nucleophilic anion, selected from the group $(BF_4)^-$, $(SbF_6)^-$, $(PF_6)^-$, $(B(C_6F_5))_4^-$, $C_1$–$C_{20}$alkylsulfonate, $C_2$–$C_{20}$haloalkylsulfonate, unsubstituted $C_6$–$C_{10}$arylsulfonate, camphorsulfonate, $C_1$–$C_{20}$-perfluoroalkylsulfonylmethide, $C_1$–$C_{20}$-perfluoroalkylsulfonylimide, and $C_6$–$C_{10}$arylsulfonate substituted by halogen, $NO_2$, $C_1$–$C_{12}$alkyl, $C_1$–$C_{12}$haloalkyl, $C_1$–$C_{12}$alkoxy or by $COOR_1$; and
$R_1$ is $C_1$–$C_{20}$alkyl, phenyl, benzyl; or phenyl mono- or poly-substituted by $C_1$–$C_{12}$alkyl, $C_1$–$C_{12}$alkoxy or by halogen;
with the proviso that the two phenyl rings on the iodine atom are not identically substituted; have an optimum balance between high sensitivity, good storage stability, good solubility and a low tendency to crystallise.

Linear $C_1$–$C_{20}$alkyl is, for example, $C_1$–$C_{12}$-, $C_1$–$C_8$-, $C_1$–$C_6$- or $C_1$–$C_4$-alkyl. Examples thereof include methyl, ethyl, propyl, n-butyl, n-pentyl, n-hexyl, n-heptyl, n-octyl, n-nonyl, n-decyl, n-undecyl, n-dodecyl, n-tetradecyl, n-pentadecyl, n-hexadecyl, n-heptadecyl, n-octadecyl, n-nonadecyl and n-icosyl. For example, Y is $C_1$–$C_8$alkyl, especially $C_1$–$C_6$alkyl, preferably $C_1$–$C_4$alkyl, such as, for example, methyl or n-butyl. Special preference is given to methyl.

Branched $C_3$–$C_{20}$alkyl is, for example, $C_3$–$C_{12}$-, $C_3$–$C_8$-, $C_3$–$C_6$- or $C_3$–$C_4$-alkyl. Examples thereof include branched propyl, such as isopropyl, branched butyl, such as sec-butyl, isobutyl or tert-butyl, branched pentyl, such as 2-methylbutyl, 3-methylbutyl or 1-methylbutyl, branched hexyl, such as 1-methylpentyl, 2-methylpentyl or 4-methylpentyl, branched heptyl, such as 1-methylhexyl, 1-ethylpentyl, 4-ethylpentyl, 1-methylhexyl or 5-methylhexyl, branched octyl, such as 2,4,4-trimethylpentyl, 2-ethylhexyl or 1-methylheptyl, branched nonyl, branched decyl, branched undecyl, branched dodecyl, branched tetradecyl, branched pentadecyl, branched hexadecyl, branched heptadecyl, branched octadecyl, branched nonadecyl and branched icosyl. For example, Y is branched $C_3$–$C_8$alkyl, especially branched $C_3$–$C_6$alkyl, preferably branched $C_3$–$C_4$alkyl, such as, for example, isopropyl, sec-butyl, isobutyl or tert-butyl.

Branched $C_4$–$C_{20}$alkyl can have the above-mentioned meanings up to the corresponding number of carbon atoms. X is, for example, $C_4$–$C_{12}$- or $C_4$–$C_8$-alkyl, such as sec-butyl, isobutyl, tert-butyl or tert-amyl, especially isobutyl or tert-amyl.

$C_1$–$C_{20}$Alkyl is linear or branched and is, for example, $C_1$–$C_{12}$-, $C_1$–$C_8$-, $C_1$–$C_6$- or $C_1$–$C_4$-alkyl. Examples thereof include methyl, ethyl, propyl, isopropyl, n-butyl, sec-butyl, isobutyl, tert-butyl, pentyl, hexyl, heptyl, 2,4,4-trimethylpentyl, 2-ethylhexyl, octyl, nonyl, decyl, undecyl, dodecyl, tetradecyl, pentadecyl, hexadecyl, heptadecyl, octadecyl, nonadecyl and icosyl. $C_1$–$C_{12}$Alkyl is likewise linear or branched and has the above-mentioned meanings up to the corresponding number of carbon atoms.

$C_3$–$C_8$Cycloalkyl is, for example, cyclopropyl, cyclopentyl, cyclohexyl or cyclooctyl, especially cyclopentyl or cyclohexyl, preferably cyclohexyl.

Halogen is fluorine, chlorine, bromine or iodine, especially chlorine or fluorine, preferably fluorine.

$C_1$–$C_{20}$Haloalkyl is a mono- or poly-halo-substituted $C_1$–$C_{20}$alkyl. The alkyl moiety can be substituted by a plurality of identical halogen atoms or, alternatively, by different halogen atoms. When $C_1$–$C_{20}$alkyl is mono- or poly-halo-substituted, there are, for example, from 1 to 3, or 1 or 2, halogen substituents present on the alkyl moiety.

$C_1$–$C_{20}$Alkylsulfonate is $RSO_3^-$ wherein R is linear or branched $C_1$–$C_{20}$alkyl as described above. Examples thereof include methylsulfonate, ethylsulfonate, propylsulfonate, pentylsulfonate and hexylsulfonate.

$C_2$–$C_{20}$Haloalkylsulfonate is $RSO_3^-$ wherein R is halo-substituted $C_2$–$C_{20}$alkyl, $C_2$–$C_{10}$-, $C_2$–$C_8$- or $C_4$–$C_8$-alkyl. Examples thereof include $C_2F_5SO_3^-$, $C_4F_9SO_3^-$ and $C_8F_{17}SO_3^-$.

Unsubstituted $C_6$–$C_{10}$arylsulfonate is $RSO_3^-$ wherein R is $C_6$–$C_{10}$aryl, e.g. phenyl or naphthyl.

Alkyl-substituted arylsulfonates are, for example, toluenesulfonate, 2,4,6-trimethylbenzenesulfonate, 2,4,6-tris(isopropyl)benzenesulfonate, 4-tert-butylbenzenesulfonate and 4-dodecylbenzenesulfonate.

Halo-substituted arylsulfonates are, for example, 4-chlorobenzenesulfonate, 4-fluorobenzenesulfonate, 2,4,6-trifluorobenzenesulfonate and pentafluorobenzenesulfonate.

Camphorsulfonate is

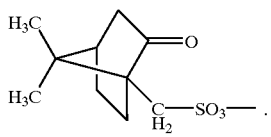

$C_1$–$C_{12}$Alkoxy denotes linear or branched radicals and is, for example, $C_1$–$C_8$-, $C_1$–$C_6$- or $C_1$–$C_4$-alkoxy. Examples thereof include methoxy, ethoxy, propoxy, isopropoxy, n-butyloxy, sec-butyloxy, isobutyloxy, tert-butyloxy, pentyloxy, hexyloxy, heptyloxy, 2,4,4-trimethylpentyloxy, 2-ethylhexyloxy, octyloxy, nonyloxy, decyloxy and dodecyloxy, especially methoxy, ethoxy, propoxy, isopropoxy, n-butyloxy, sec-butyloxy, isobutyloxy and tert-butyloxy, preferably methoxy.

Mono- or poly-substituted phenyl is mono- to penta-substituted, for example mono-, di- or tri-substituted, especially mono- or di-substituted.

$C_1$–$C_{20}$-Perfluoroalkylsulfonylmethide is

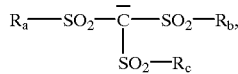

$C_1$–$C_{20}$-perfluoroalkylsulfonylimide is $R_a$—$SO_2$—$\overline{N}$—$SO_2$—$R_b$, wherein $R_a$, $R_b$ and $R_c$ independently of one another are $C_1$–$C_{20}$perfluoroalkyl which is unsubstituted or is substituted by $N(R_d)(R_e)$, or $R_a$, $R_b$ and $R_c$ are phenyl substituted by $CF_3$; or $R_a$ and $R_b$ together are $C_1$–$C_6$-perfluoroalkylene, which optionally is interrupted by —O—; $R_d$ and $R_e$ independently of one another are $C_1$–$C_{12}$alkyl or $R_d$ and $R_e$ together are $C_1$–$C_6$perfluorolkylene, which optionally is interrupted by O or $N(C_1$–$C_{12}$-Alkyl). Perfluoroalkyl is alkyl which is fully substituted by fluoro, i.e. the hydrogen atoms are replaced by fluoro. The same applies for the perfluoroalkylene.

Examples of such anions are $(C_2F_5SO_2)_2N^-$, $(C_4F_9SO_2)_2N^-$, $(C_8F_{17}SO_2)_3C^-$, $(CF_3SO_2)_3C^-$, $(CF_3SO_2)_2N^-$, $(C_4F_9SO_2)_3C^-$, $(CF_3SO_2)_2(C_4F_9SO_2)C^-$, $(CF_3SO_2)_2(C_4F_9SO_2)C^-$, $(CF_3SO_2)(C_4F_9SO_2)N^-$, $[(3,5\text{-bis}(CF_3)\text{-}(C_6H_3)SO_2]_2N^-$,

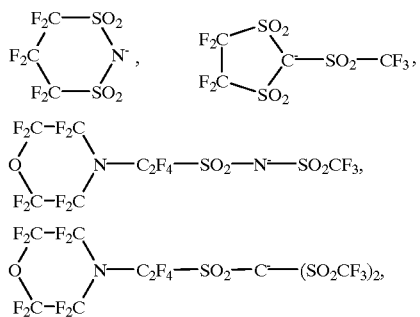

$C_6F_5SO_2C^-(SO_2CF_3)_2$, $C_6F_5SO_2N^-SO_2CF_3$.

Such anions are known the person skilled in the art. The anions as well as their preparation are described e.g. in U.S. Pat. No. 5,554,664.

The position of the radicals X and Y on the phenyl rings of the iodonium salt compound of formula I is, for example, in the 4,4'-position, the 4,2'-position or the 4,3'-position, especially in the 4,4'-position or in the 4,2'-position, preferably in the 4,4'-position.

The position of the radicals X, $X_1$ and Y on the phenyl rings of the iodonium salt compound of formula I is, for example, in the 2,4,4'-position, 2,4,2'-position or the 2,4,3'-position, especially in the 2,4,4'-position or the 2,4,2'-position, preferably in the 2,4,4'-position.

X is branched $C_3$–$C_{20}$alkyl or $C_3$–$C_8$cycloalkyl, preferably branched $C_3$–$C_8$alkyl, cyclohexyl or cyclopentyl, especially branched $C_3$–$C_4$alkyl or cyclohexyl, for example isopropyl, isobutyl, sec-butyl or tert-butyl.

$X_1$ is hydrogen, linear $C_1$–$C_{20}$alkyl, branched $C_3$–$C_{20}$alkyl or $C_3$–$C_8$cycloalkyl, preferably hydrogen, linear $C_1$–$C_{10}$alkyl, branched $C_3$–$C_8$alkyl, especially hydrogen or branched $C_3$–$C_4$-alkyl. $X_1$ is especially preferably hydrogen.

The sum of the carbon atoms in the substituents X and $X_1$ in the compounds according to the invention is always at least 4, that is to say the sum is 4 or greater than 4, for example from 4 to 40, from 4 to 20, from 4 to 10, from 4 to 8, from 5 to 40, from 6 to 40, etc.

Y is linear $C_1$–$C_{10}$alkyl, branched $C_3$–$C_{10}$alkyl or $C_3$–$C_8$cycloalkyl, preferably linear $C_1$–$C_8$- or linear $C_1$–$C_6$-alkyl, branched $C_3$–$C_8$- or branched $C_3$–$C_6$-alkyl, cyclohexyl or cyclopentyl, for example isopropyl or linear $C_1$–$C_4$alkyl.

A is a non-nucleophilic anion, selected from the group $(BF_4)^-$, $(SbF_6)^-$, $(PF_6)^-$, $(B(C_6F_5))_4^-$, $C_1$–$C_{20}$alkylsulfonate, $C_2$–$C_{20}$haloalkylsulfonate, unsubstituted $C_6$–$C_{10}$arylsulfonate, camphorsulfonate, $C_1$–$C_{20}$-perfluoroalkylsulfonylmethide, $C_1$–$C_{20}$-perfluoroalkylsulfonylimide, and $C_6$–$C_{10}$-arylsulfonate substituted by halogen, $NO_2$, $C_1$–$C_{12}$alkyl, $C_1$–$C_{12}$halo-alkyl, $C_1$–$C_{12}$alkoxy or by $COOR_1$; e.g. selected from the group $(SbF_6)^-$, $(PF_6)^-$, $(B(C_6F_5))_4^-$, $C_2$–$C_{20}$haloalkylsulfonate, camphorsulfonate, $C_1$–$C_{12}$alkylsulfonate, phenylsulfonate and p-methylphenylsulfonate; especially selected from the group $(SbF_6)^-$, $(PF_6)^-$, $(B(C_6F_5))_4^-$ and $C_2$–$C_{20}$haloalkylsulfonate.

A characterising feature of the compounds of formula I according to the invention is that the two phenyl rings on the iodine atom are not identically substituted, that is to say they are "asymmetric" iodonium salts. X or $X_1$ and Y are thus different in each case. It is also to be noted that one phenyl ring is always substituted at least by a branched alkyl group or by cycloalkyl, with the branched alkyl X being at least a $C_4$alkyl when $X_1$ is hydrogen. When $X_1$ is other than hydrogen, the branched alkyl X can also be a $C_3$alkyl. The sum of the carbon atoms of the radicals $X+X_1$ is thus always at least 4. A further feature of the compounds according to the invention is that both phenyl rings on the iodine atom must carry substituents, so that the formation of benzene upon cleavage is avoided.

The compounds according to the invention offer an optimum balance between the requisite reactivity for a very wide range of applications (as described below and in the Examples) and good solubility in the formulations, and they prevent the release of benzene. Also, relatively low toxicological effect is to be expected as a result of the substitution.

General processes for the preparation of aryliodonium salt compounds are known to the person skilled in the art and are described in the literature. The photoinitiator compounds of formula I according to the invention can be obtained analogously to those processes. For example, compounds of formula I can be prepared according to the processes described in U.S. Pat. Nos. 4,399,071 and 4,329,300 and in DE 2,754,853. For example, it is possible to prepare the hexafluorophosphate salts by exchanging the anions from the simple salts of the corresponding iodonium compounds (such as the bissulfates). Those methods have been published, for example, by Beringer et al. in J. Am. Chem. Soc. 81, 342 (1959). Various methods for the preparation of the above-mentioned simple salts can also be found in that literature reference. For example, the reaction of two aromatic compounds with iodyl sulfate in sulfuric acid, the reaction of two aromatic compounds with iodate in acetic acid, acetic anhydride, sulfuric acid, the reaction of two aromatic compounds with iodoacylate in the presence of an acid, or the condensation of an iodoso compound, an iodoso diacetate or an iodoxy compound with a different aromatic compound in the presence of an acid.

In some cases it is also possible to oxidise an aryl iodide in situ, and then condense it with the other aromatic compound. That variant of the condensation is carried out, for example, in dilute sulfuric acid (EP 119068).

Preference is given to radiation-sensitive compositions wherein in the compounds of formula I X is branched $C_4$–$Cl_2$alkyl or cyclohexyl.

Further compositions of interest are those wherein in the compounds of formula I Y is linear $C_1$–$C_6$alkyl or cyclohexyl.

Special emphasis is given to compositions according to the invention wherein in the compounds of formula I $A^-$ is a non-nucleophilic anion, selected from the group $(PF_6)^-$, $(B(C_6F_5))_4^-$, $C_1$–$C_{12}$alkylsulfonate, $C_2$–$C_{12}$haloalkylsulfonate, unsubstituted phenylsulfonate, camphorsulfonate, $C_1$–$C_{20}$-perfluoroalkylsulfonylmethide, $C_1$–$C_{20}$-perfluoroalkylsulfonylimide, and phenylsulfonate substituted by halogen, $NO_2$, $C_1$–$C_{12}$alkyl, $C_1$–$C_{12}$-haloalkyl, $C_1$–$C_{12}$alkoxy or by $COOR_1$, in particular $A^-$ is a non-nucleophilic anion, selected from the group $(PF_6)^-$, $(B(C_6F_5))_4^-$, $C_1$–$C_{12}$alkylsulfonate, $C_2$–$C_{12}$haloalkylsulfonate, unsubstituted phenylsulfonate, camphorsulfonate, and phenylsulfonate substituted by halogen, $NO_2$, $C_1$–$C_{12}$alkyl, $C_1$–$C_{12}$-haloalkyl, $C_1$–$C_{12}$alkoxy or by $COOR_1$.

Special preference is given to radiation-sensitive compositions wherein in the compounds of formula I X is branched $C_4$–$C_6$alkyl or cyclohexyl;

$X_1$ is hydrogen or branched $C_4$–$C_6$alkyl;

Y is linear $C_1$–$C_4$alkyl, branched $C_3$–$C_4$alkyl or cyclohexyl;

$A^-$ is a non-nucleophilic anion, selected from the group $(PF_6)^-$, camphorsulfonate and $C_1$–$C_4$alkyl-substituted phenylsulfonate.

Also of interest are compositions wherein in the compounds of formula I

X is branched $C_4$–$C_6$alkyl or cyclohexyl;

Y is linear $C_1$–$C_4$alkyl, branched $C_3$–$C_4$alkyl or cyclohexyl;

$A^-$ is a non-nucleophilic anion, selected from the group $(PF_6)^-$, $(B(C_6F_5))_4^-$, $C_1$–$C_{20}$-alkylsulfonate, $C_1$–$C_{20}$haloalkylsulfonate, unsubstituted $C_6$–$C_{10}$arylsulfonate, camphorsulfonate, and $C_6$–$C_{10}$arylsulfonate substituted by halogen, $NO_2$, $C_1$–$C_{12}$alkyl, $C_1$–$C_{12}$halo-alkyl, $C_1$–$C_{12}$alkoxy or by $COOR_1$; and $R_1$ is $C_1$–$C_{12}$alkyl, phenyl, benzyl, or phenyl mono- or poly-substituted by $C_1$–$C_4$alkyl.

Examples of compounds of formula I suitable as component (b) in the compositions according to the invention include 4-isobutylphenyl-4'-methylphenyliodonium hexafluoro-phosphate; 4-isobutylphenyl-4'-methylphenyliodonium pentafluoroethylsulfonate; 4-isobutylphenyl-4'-methylphenyliodonium tresylate; 4-isobutylphenyl-4'-methylphenyliodonium nonaflate; 4-isobutylphenyl-4'-methylphenyliodonium tosylate; 4-isobutylphenyl-4'-methyl-phenyliodonium 4-methoxyphenylsulfonate; 4-isobutylphenyl-4'-methylphenyliodonium 4-chlorophenylsulfonate; 4-isobutylphenyl-4'-methylphenyliodonium 4-fluorophenylsulfonate; 4-isobutylphenyl-4'-methylphenyliodonium 2,4,6-trimethylphenylsulfonate; 4-isobutylphenyl-4'-methylphenyliodonium 2,4,6-(triisopropyl)-phenylsulfonate; 4-isobutylphenyl-4'-methyl-phenyliodonium 4-dodecylphenylsulfonate; 4-isobutylphenyl-4'-methylphenyliodonium camphor-10-sulfonate; 4-isobutylphenyl-4'-methylphenyliodonium tetrakis(pentafluorophenyl)-borate; 4-(2-methylbut-2-yl)-phenyl-4'-methylphenyliodonium hexafluorophosphate; 4-(2-methylbut-2-yl)phenyl-4'-methyl-phenyliodonium pentafluoroethylsulfonate; 4-(2-methylbut-2-yl)phenyl-4'-methylphenyliodonium tetrakis(pentafluorophenyl)borate; 4-(2-methylbut-2-yl)phenyl-4'-methylphenyliodonium hexafluorophosphate; 4-(2-methylbut-2-yl)phenyl-4'-methylphenyliodonium pentafluoroethylsulfonate; 4-(2-methylbut-2-yl)phenyl-4'-methyl-phenyliodonium nonaflate; 4-(2-methylbut-2-yl)phenyl-4'-methylphenyliodonium 4-trifluoro-methylphenylsulfonate; 4-(2-methylbut-2-yl)-phenyl-4'-methylphenyliodonium tosylate; 4-(2-methylbut-2-yl)phenyl-4'-methylphenyliodonium camphor-10-sulfonate; 4-cyclohexyl-4'-methylphenyliodonium hexafluorophosphate; 4-cyclohexyl-4'-methylphenyliodonium pentafluoroethylsulfonate; 4-cyclohexyl-4'-methylphenyliodonium camphor-10-sulfonate; 4-cyclohexyl-4'-methylphenyliodonium tetrakis(pentafluorophenyl)borate; 4-cyclohexyl-4'-methyl-phenyliodonium tosylate; 4-tert-butylphenyl-4'-methylphenyliodonium hexafluorophosphate; 4-tert-butylphenyl-4'-methylphenyliodonium pentafluoroethylsulfonate; 4-tert-butylphenyl-4'-methylphenyliodonium camphor-10-sulfonate; 4-tert-butylphenyl-4'-methylphenyliodonium tetrakis (pentafluorophenyl)borate; 4-tert-butylphenyl-4'-methylphenyliodonium 4-chloro-phenylsulfonate; 4-tert-butylphenyl-4'-methylphenyliodonium 4-fluorophenylsulfonate; 4-tert-butylphenyl-4'-methylphenyliodonium 4-methoxyphenylsulf-onate; 4-tert-butylphenyl-4'-methylphenyliodonium hexafluorophosphate; 4-isobutylphenyl-4'-methylphenyliodonium nonafluorobutylsulfonate; 4-cyclohexyl-4'-methylphenyliodonium hexafluoroantimonate; 4-(2- methylbut-2-yl)phenyl-4'-methylphenyliodonium nonafluorobutylsulfonate; 4-isobutyl-phenyl-2'-methylphenyliodonium hexafluorophosphate; 4-isobutylphenyl-4'-ethylphenyl-iodonium hexafluorophosphate; 4-(branched dodecyl)-4-methylphenyliodonium hexafluorophosphate.

The compounds of formula I, as described above, are novel and this invention accordingly relates also thereto. The preferred meanings are also as given above.

The compositions according to the invention comprise as component (a1), for example, resins and compounds that can be cationically polymerised by alkyl- or aryl-containing cations or by protons. Examples thereof include cyclic ethers, especially epoxides and oxetanes, and also vinyl ethers and hydroxy-containing compounds. Lactone compounds and cyclic thioethers as well as vinyl thioethers can also be used. Further examples include aminoplastics or phenolic resole resins. These are especially melamine, urea, epoxy, phenolic, acrylic, polyester and alkyd resins, but especially mixtures of acrylic, polyester or alkyd resins with a melamine resin. These include also modified surface-coating resins, such as, for example, acrylic-modified polyester and alkyd resins. Examples of individual types of resins that are included under the terms acrylic, polyester and alkyd resins are described, for example, in Wagner, Sarx/Lackkunstharze (Munich, 1971), pages 86 to 123 and 229 to 238, or in Ullmann/Encyclopädie der techn. Chemie, $4^{th}$ edition, volume 15 (1978), pages 613 to 628, or Ullmann's Encyclopedia of Industrial Chemistry, Verlag Chemie, 1991, Vol. 18, 360 ff., Vol. A19, 371 ff. The surface-coating preferably comprises an amino resin. Examples thereof include etherified and non-etherified melamine, urea, guanidine and biuret resins. Of special importance is acid catalysis for the curing of surface-coatings comprising etherified amino resins, such as, for example, methylated or butylated melamine resins (N-methoxymethyl- or N-butoxymethyl-melamine) or methylated/butylated glycolurils.

It is possible, for example, to use all customary epoxides, such as aromatic, aliphatic or cycloaliphatic epoxy resins. These are compounds having at least one, preferably at least two, epoxy group(s) in the molecule. Examples thereof are the glycidyl ethers and symbol 98 \f "Symbol" \s 11β-methyl glycidyl ethers of aliphatic or cycloaliphatic diols or polyols, e.g. those of ethylene glycol, propane-1,2-diol, propane-1,3-diol, butane-1,4-diol, diethylene glycol, polyethylene glycol, polypropylene glycol, glycerol, trimethylolpropane or 1,4-dimethylolcyclohexane or of 2,2-bis(4-hydroxycyclohexyl)propane and N,N-bis(2-hydroxyethyl) aniline; the glycidyl ethers of di- and poly-phenols, for example of resorcinol, of 4,4'-dihydroxyphenyl-2,2-propane, of novolaks or of 1,1,2,2-tetrakis(4-hydroxyphenyl)ethane. Examples thereof include phenyl glycidyl ether, p-tert-butyl glycidyl ether, o-icresyl glycidyl ether, polytetrahydrofuran glycidyl ether, n-butyl glycidyl ether, 2-ethylhexyl glycidyl ether, $C_{12/15}$alkyl glycidyl ether and cyclohexanedimethanol diglycidyl ether. Further examples include N-glycidyl compounds, for example the glycidyl compounds of ethyleneurea, 1,3-propyleneurea or 5-dimethyl-hydantoin or of 4,4'-methylene-5,5'-tetramethyldihydantoin, or compounds such as triglycidyl isocyanurate.

Further examples of glycidyl ether components (a1) that are used in the formulations according to the invention are, for example, glycidyl ethers of polyhydric phenols obtained by the reaction of polyhydric phenols with an excess of chlorohydrin, such as, for example, epichlorohydrin (e.g.

glycidyl ethers of 2,2-bis(2,3-epoxypropoxyphenol) propane. Further examples of glycidyl ether epoxides that can be used in connection with the present invention are described, for example, in U.S. Pat. No. 3,018,262 and in "Handbook of Epoxy Resins" by Lee and Neville, McGraw-Hill Book Co., New York (1967).

There is also a large number of commercially available glycidyl ether epoxides that are suitable as component (a1), such as, for example, glycidyl methacrylate, diglycidyl ethers of bisphenol A, for example those obtainable under the trade names EPON 828, EPON 825, EPON 1004 and EPON 1010 (Shell); DER-331, DER-332 and DER-334 (Dow Chemical); 1,4-butanediol diglycidyl ethers of phenolformaldehyde novolak, e.g. DEN-431, DEN-438 (Dow Chemical); and resorcinol diglycidyl ethers; alkyl glycidyl ethers, such as, for example, $C_8$–$C_{10}$glycidyl ethers, e.g. HELOXY Modifier 7, $C_{12}$–$C_{14}$glycidyl ethers, e.g. HELOXY Modifier 8, butyl glycidyl ethers, e.g. HELOXY Modifier 61, cresyl glycidyl ethers, e.g. HELOXY Modifier 62, p-tert-butylphenyl glycidyl ethers, e.g. HELOXY Modifier 65, polyfunctional glycidyl ethers, such as diglycidyl ethers of 1,4-butanediol, e.g. HELOXY Modifier 67, diglycidyl ethers of neopentyl glycol, e.g. HELOXY Modifier 68, diglycidyl ethers of cyclohexanedimethanol, e.g. HELOXY Modifier 107, trimethylolethane triglycidyl ethers, e.g. HELOXY Modifier 44, trimethylolpropane triglycidyl ethers, e.g. HELOXY Modifier 48, polyglycidyl ethers of aliphatic polyols, e.g. HELOXY Modifier 84 (all HELOXY glycidyl ethers are obtainable from Shell).

Also suitable are glycidyl ethers that comprise copolymers of acrylic esters, such as, for example, styrene-glycidyl methacrylate or methyl methacrylate-glycidyl acrylate. Examples thereof include 1:1 styrene/glycidyl methacrylate, 1:1 methyl methacrylate/glycidyl acrylate, 62.5:24:13.5 methyl methacrylate/ethyl acrylate/glycidyl methacrylate.

The polymers of the glycidyl ether compounds can, for example, also comprise other functionalities provided that these do not impair the cationic curing.

Other glycidyl ether compounds suitable as component (a1) that are commercially available from Ciba Specialty Chemicals are polyfunctional liquid and solid novolak glycidyl ether resins, e.g. PY 307, EPN 1179, EPN 1180, EPN 1182 and ECN 9699.

It will be understood that mixtures of different glycidyl ether compounds may also be used as component (a1).

The glycidyl ethers (a1) are, for example, compounds of formula II

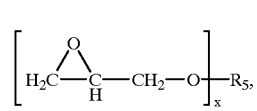
(II)

x is a number from 1 to 6; and
$R_5$ is a mono- to hexa-valent alkyl or aryl radical.

Preference is given, for example, to glycidyl ether compounds of formula II

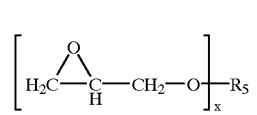
(II)

x is the number 1, 2 or 3; and
$R_5$ when x =1, is unsubstituted or $C_1$–$C_{12}$alkyl-substituted phenyl, naphthyl, anthracyl, biphenylyl, $C_1$–$C_{20}$alkyl, or $C_2$–$C_{20}$alkyl interrupted by one or more oxygen atoms, or $R_5$ when x=2, is 1,3-phenylene, 1,4-phenylene, $C_6$–$C_{10}$cycloalkylene, unsubstituted or halo-substituted $C_1$–$C_{40}$alkylene, $C_2$–$C_{40}$alkylene interrupted by one or more oxygen atoms, or a group

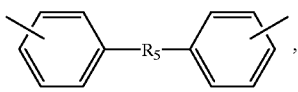

or $R_5$ when x=3, is a radical

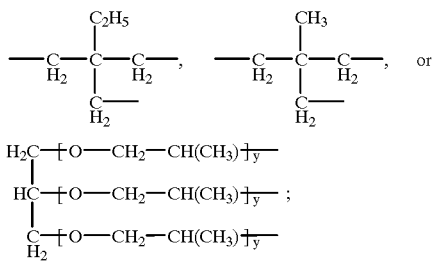

y is a number from 1 to 10; and $R_6$ is $C_1$–$C_{20}$alkylene, oxygen or

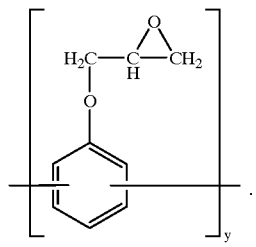

The glycidyl ethers (a1) are, for example, compounds of formula IIa

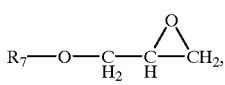
(IIa)

wherein $R_7$ is unsubstituted or $C_1$–$C_{12}$alkyl-substituted phenyl; naphthyl; anthracyl; biphenylyl; $C_1$–$C_{20}$alkyl, $C_2$–$C_{20}$alkyl interrupted by one or more oxygen atoms; or a group of formula

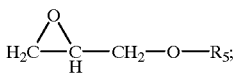

$R_5$ is phenylene, $C_1$–$C_{20}$alkylene, $C_2$–$C_{20}$alkylene interrupted by one or more oxygen atoms, or a group

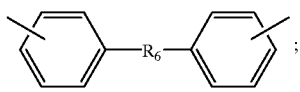

and $R_6$ is $C_1$–$C_{20}$alkylene or oxygen.

Preference is given to the glycidyl ether compounds of formula IIb

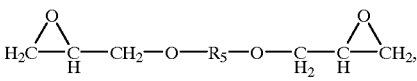
(IIb)

wherein $R_5$ is phenylene, $C_1$–$C_{20}$alkylene, $C_2$–$C_{20}$alkylene interrupted by one or more oxygen atoms,

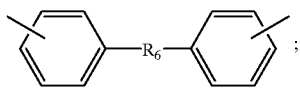

and $R_6$ is $C_1$–$C_{20}$alkylene or oxygen.

Further examples for component (a1) are polyglycidyl ethers and poly(β-methylglycidyl) ethers obtainable by the reaction of a compound containing at least two free alcoholic and/or phenolic hydroxy groups per molecule with the appropriate epichlorohydrin under alkaline conditions, or alternatively in the presence of an acid catalyst with subsequent alkali treatment. Mixtures of different polyols may also be used.

Such ethers can be prepared with poly(epichlorohydrin) from acyclic alcohols, such as ethylene glycol, diethylene glycol and higher poly(oxyethylene) glycols, propane-1,2-diol and poly(oxypropylene) glycols, propane-1,3-diol, butane-1,4-diol, poly(oxytetramethylene) glycols, pentane-1,5-diol, hexane-1,6-diol, hexane-2,4,6-triol, glycerol, 1,1,1-trimethylol-propane, pentaerythritol and sorbitol, from cycloaliphatic alcohols, such as resorcitol, quinitol, bis(4-hydroxycyclohexyl)methane, 2,2-bis(4-hydroxycyclohexyl) propane and 1,1-bis-(hydroxymethyl)cyclohex-3-ene, and from alcohols having aromatic nuclei, such as N,N-bis(2-hydroxyethyl)aniline and p,p'-bis(2-hydroxyethylamino) diphenylmethane. They can also be prepared from mononuclear phenols, such as resorcinol and hydroquinone, and polynuclear phenols, such as bis(4-hydroxyphenyl)methane, 4,4-dihydroxydiphenyl, bis(4-hydroxyphen-yl)sulfone, 1,1,2,2-tetrakis(4-hydroxyphenyl)ethane, 2,2-bis(4-hydroxyphenyl)-propane (bisphenol A) and 2,2-bis(3,5-dibromo-4-hydroxyphenyl)propane.

Further hydroxy compounds suitable for the preparation of polyglycidyl ethers and poly(β-methylglycidyl) ethers are the novolaks obtainable by the condensation of aldehydes, such as formaldehyde, acetaldehyde, chloral and furfural, with phenols, such as, for example, phenol, o-cresol, m-cresol, p-cresol, 3,5-dimethylphenol, 4-chlorophenol and 4-tert-butylphenol.

Poly(N-glycidyl) compounds can be obtained, for example, by dehydrochlorination of the reaction products of epichlorohydrin with amines containing at least two amino-hydrogen atoms, such as aniline, n-butylamine, bis(4-aminophenyl)methane, bis(4-aminophenyl)-propane, bis-(4-methylaminophenyl)methane and bis(4-aminophenyl) ether, sulfone and sulfoxide. Further suitable poly(N-glycidyl) compounds include triglycidyl isocyanurate, and N,N'-diglycidyl derivatives of cyclic alkyleneureas, such as ethyleneurea and 1,3-propyleneurea, and hydantoins, such as, for example, 5,5-dimethylhydantoin.

Poly(S-glycidyl) compounds are also suitable. Examples thereof include the di-S-glycidyl derivatives of dithiols, such as ethane-1,2-dithiol and bis(4-mercaptomethylphenyl) ether.

There also come into consideration as component (a1) epoxy resins in which the glycidyl groups or β-methyl glycidyl groups are bonded to hetero atoms of different types, for example the N,N,O-triglycidyl derivative of 4-aminophenol, the glycidyl ether/glycidyl ester of salicylic acid or p-hydroxybenzoic acid, N-glycidyl-N'-(2-glycidyloxypropyl)-5,5-dimethyl-hydantoin and 2-glycidyloxy-1,3-bis(5,5-dimethyl-1-glycidylhydantoin-3-yl)propane.

Preference is given to diglycidyl ethers of bisphenols. Examples thereof include diglycidyl ethers of bisphenol A, e.g. ARALDIT GY 250 from Ciba Specialty Chemicals, diglycidyl ethers of bisphenol F and diglycidyl ethers of bisphenol S. Special preference is given to diglycidyl ethers of bisphenol A.

Further glycidyl compounds of technical importance are the glycidyl esters of carboxylic acids, especially di- and poly-carboxylic acids. Examples thereof are the glycidyl esters of succinic acid, adipic acid, azelaic acid, sebacic acid, phthalic acid, terephthalic acid, tetra- and hexa-hydrophthalic acid, isophthalic acid or trimellitic acid, or of dimerised fatty acids.

Examples of polyepoxides that are not glycidyl compounds are the epoxides of vinylcyclohexane and dicyclopentadiene, 3-(3',4'-epoxycyclohexyl)-8,9-epoxy-2,4-dioxaspiro-[5.5]-undecane, the 3',4'-epoxycyclohexylmethyl esters of 3,4-epoxycyclohexanecarboxylic acid, (3,4-epoxycyclohexyl-methyl 3,4-epoxycyclohexanecarboxylate), butadiene diepoxide or isoprene diepoxide, epoxidised linoleic acid derivatives or epoxidised polybutadiene.

Further suitable epoxy compounds are, for example, limonene monoxide, epoxidised soybean oil, bisphenol-A and bisphenol-F epoxy resins, such as, for example, Araldit® GY 250 (A), Araldit® GY 282 (F), Araldit® GY 285 (F) (Ciba Specialty Chemicals), and photocurable siloxanes that contain epoxy groups.

Further suitable cationically polymerisable or crosslinkable components (a1) can be found, for example, also in U.S. Pat. Nos. 3,117,099, 4,299,938 and 4,339,567.

From the group of aliphatic epoxides there are suitable especially the monofunctional symbol α-olefin epoxides having an unbranched chain consisting of 10, 12, 14 or 16 carbon atoms.

Because nowadays a large number of different epoxy compounds are commercially available, the properties of the binder can vary widely. One possible variation, for example depending upon the intended use of the composition, is the use of mixtures of different epoxy compounds and the addition of flexibilisers and reactive diluents.

The epoxy resins can be diluted with a solvent to facilitate application, for example when application is effected by spraying, but the epoxy compound is preferably used in the solventless state. Resins that are viscous to solid at room temperature can be applied hot.

Also suitable as component (a1) are all customary vinyl ethers, such as aromatic, aliphatic or cycloaliphatic vinyl ethers and also silicon-containing vinyl ethers. These are compounds having at least one, preferably at least two, vinyl ether groups in the molecule. Examples of vinyl ethers suitable for use in the compositions according to the invention include triethylene glycol divinyl ether, 1,4-cyclohexanedimethanol divinyl ether, 4-hydroxybutyl vinyl ether, the propenyl ether of propylene carbonate, dodecyl vinyl ether, tert-butyl vinyl ether, tert-amyl vinyl ether, cyclohexyl vinyl ether, 2-ethylhexyl vinyl ether, ethylene glycol monovinyl ether, butanediol monovinyl ether, hexanediol monovinyl ether, 1,4-cyclohexanedimethanol monovinyl ether, diethylene glycol monovinyl ether, ethylene glycol divinyl ether, ethylene glycol butylvinyl ether, butane-1,4-diol divinyl ether, hexanediol divinyl ether, diethylene glycol divinyl ether, triethylene glycol divinyl ether, triethylene glycol methylvinyl ether, tetra-ethylene glycol divinyl ether, pluriol-E-200 divinyl ether, polytetrahydrofuran divinyl ether-290, trimethylolpropane trivinyl ether, dipropylene glycol divinyl ether, octadecyl vinyl ether, (4-cyclohexyl-methyleneoxyethene)-glutaric acid methyl ester and (4-butoxyethene)-iso-phthalic acid ester.

Examples of hydroxy-containing compounds include polyester polyols, such as, for example, polycaprolactones or polyester adipate polyols, glycols and polyether polyols, castor oil, hydroxy-functional vinyl and acrylic resins, cellulose esters, such as cellulose acetate butyrate, and phenoxy resins.

Further cationically curable formulations can be found, for example, in EP 119425.

As component (a1), preference is given to cycloaliphatic epoxides, or epoxides based on bisphenol A.

Accordingly, the invention relates also to a radiation-sensitive composition wherein component (a1) is at least one compound selected from the group of cycloaliphatic epoxy compounds, glycidyl ethers, oxetane compounds, vinyl ethers, acid-crosslinkable melamine resins, acid-crosslinkable hydroxymethylene compounds and acid-crosslinkable alkoxymethylene compounds.

If desired, the composition according to the invention can also contain free-radically polymerisable components, such as ethylenically unsaturated monomers, oligomers or polymers. Suitable materials contain at least one ethylenically unsaturated double bond and are capable of undergoing addition polymerisation.

Examples of suitable monomers that contain an ethylenic double bond include alkyl and hydroxyalkyl acrylates and methacrylates, such as methyl, ethyl, propyl, isopropyl, butyl, hexyl, 2-ethylhexyl and 2-hydroxyethyl (meth)acrylate, stearyl acrylate and isobornyl acrylates. Further suitable examples include acrylonitrile, acrylamide, methacrylamide, N-substituted (meth)acrylamides, vinyl esters, such as vinyl acetate, vinyl ethers, such as isobutylvinyl ether, styrene, alkyl- and halo-substituted styrene, N-vinylpyrrolidone, vinyl chloride and vinylidene chloride.

Examples of suitable monomers that contain at least two double bonds include glycerol diacrylates, glycerol triacrylates, ethylene glycol diacrylates, diethylene glycol diacrylates, diethylene glycol dimethacrylate, triethylene glycol dimethacrylates, 1,3-propanediol di-acrylate, 1,3-propanediol dimethacrylate, neopentyl glycol diacrylates, hexamethylene glycol diacrylate, bisphenol-A diacrylates, 4,4'-bis(2-acryloyloxyethoxy)diphenylpropane, pentaerythritol triacrylate or tetraacrylate, pentaerythritol tetramethacrylate, trimethylolpropane triacrylate, 1,2,4-butanetriol trimethacrylate, 1,4-cyclohexanediol diacrylate, sorbitol hexa-acrylate, bis[1-(2-acryloxy)]-p-ethoxyphenyldimethylmethane, bis[1-(3-acryloxy-2-hydroxy)]-p-propoxyphenyidimethylmethane and trishydroxyethyl isocyanurate trimethacrylate; the bis-acrylates and bis-methacrylates of poly(ethylene glycol) having a molecular weight of from 200 to 500, diallyl phthalate, divinyl succinate, divinyl adipate and divinyl phthalate, vinyl acrylate, divinyl benzene, triallyl phosphate, triallyl isocyanurates and tris(2-acryloyl-ethyl) isocyanurate.

Examples of higher-molecular-weight (oligomeric) poly-unsaturated compounds include acrylated epoxy resins, acrylated or vinyl ether- or epoxy-group-containing polyesters, polyurethanes and polyethers. Further examples of unsaturated oligomers are unsaturated polyester resins, which are usually prepared from maleic acid, phthalic acid and one or more diols and have molecular weights of approximately from 500 to 3000. Vinyl ether monomers and oligomers, and maleate-terminated oligomers having polyester, poly-urethane, polyether, polyvinyl ether and epoxy main chains can also be used. Also copolymers of vinyl ethers and monomers which are functionalised with maleic acid, as described in WO 90/01512, are also very suitable. Also suitable, however, are copolymers of monomers functionalised with vinyl ether and maleic acid. Such unsaturated oligomers can also be referred to as pre-polymers.

Functionalised acrylates are also suitable. Examples of suitable monomers that are normally used to form the base polymer (the backbone) of the functionalised acrylate or methacrylate polymer are acrylate, methacrylate, methyl methacrylate, ethyl acrylate, ethyl methacrylate, n-butyl acrylate, n-butyl methacrylate, isobutyl acrylate, isobutyl methacrylate, 2-ethylhexyl acrylate, 2-ethylhexyl methacrylate, etc. In addition, suitable amounts of functional monomers are copolymerised during the polymerisation in order to obtain the functional polymers. Acid-functionalised acrylate or methacrylate polymers are obtained using acid-functional monomers, such as acrylic acid and methacrylic acid. Hydroxy-functional acrylate or methacrylate polymers are obtained from hydroxy-functional monomers, such as 2-hydroxyethyl methacrylate, 2-hydroxypropyl methacrylate and 3,4-dihydroxybutyl meth-acrylate. Epoxy-functionalised acrylate or methacrylate polymers are obtained using epoxy-functional monomers, such as gly-cidyl methacrylate, 2,3-epoxybutyl methacrylate, 3,4-epoxybutyl methacrylate, 2,3-epoxycyclohexyl methacrylate, 10,11-epoxyundecyl meth-acrylate, etc. It is also possible to obtain isocyanate-functional polymers from isocyanate-functionalised monomers, such as meta-isopropenyl-α,(α-dimethylbenzyl isocyanate.

Especially suitable are, for example, esters of etheleni-cally unsaturated mono- or poly-functional carboxylic acids and polyols or polyepoxides, and polymers having ethyleni-cally unsaturated groups in the chain or in side groups, such as unsaturated polyesters, polyamides and polyurethanes and copolymers thereof, alkyd resins, polybutadiene and butadiene copolymers, polyisoprene and isoprene copolymers, polymers and copolymers having (meth)acrylic groups in side chains, and mixtures of one or more such polymers.

Examples of suitable mono- or poly-functional unsaturated carboxylic acids are acrylic acid, methacrylic acid, crotonic acid, itaconic acid, cinnamic acid, maleic acid and fumaric acid and unsaturated fatty acids, such as linolenic acid or oleic acid. Preference is given to acrylic acid and methacrylic acid.

Mixtures of saturated di- or poly-carboxylic acids with unsaturated carboxylic acids may, however, also be used. Examples of suitable saturated di- or poly-carboxylic acids include, for example, tetrachlorophthalic acid, tetrabro-mophthalic acid, phthalic acid anhydride, adipic acid, tet-rahydrophthalic acid, isophthalic acid, terephthalic acid, trimellitic acid, heptanedicarboxylic acid, sebacic acid, dodecanedicarboxylic acid, hexahydrophthalic acid, etc.

Suitable polyols are aromatic and especially aliphatic and cycloaliphatic polyols. Examples of aromatic polyols are hydroquinone, 4,4'-dihydroxydiphenyl, 2,2-di(4-hydroxyphenyl)-propane, and novolaks and resoles. Examples of polyepoxides are those based on the polyols mentioned, especially the aromatic polyols and epichloro-hydrin. Also suitable as polyols are polymers and copolymers containing hydroxyl groups in the polymer chain or in side groups, such as polyvinyl alcohol and copolymers thereof or polymethacrylic acid hydroxyalkyl esters or copolymers thereof. Further suitable polyols are oligoesters having hydroxyl terminal groups.

Examples of aliphatic and cycloaliphatic polyols are alkylenediols having preferably from 2 to 12 carbon atoms, such as ethylene glycol, 1,2- or 1,3-propanediol, 1,2-, 1,3- or 1,4-butanediol, pentanediol, hexanediol, octanediol, dodecanediol, diethylene glycol, triethylene glycol, polyethylene glycols having molecular weights of preferably from 200 to 1500, 1,3-cyclopentanediol, 1,2-, 1,3- or 1,4-cyclohexanediol, 1,4-dihydroxymethylcyclohexane, glycerol, tris(β-hydroxyethyl)amine, trimethylolethane, trimethylolpropane, pentaerythritol, dipentaerythritol and sorbitol.

The polyols may be partially or fully esterified by one or by different unsaturated carboxylic acid(s), it being possible for the free hydroxyl groups in partial esters to have been modified, for example etherified, or esterified by other carboxylic acids.

Examples of esters are:
trimethylolpropane triacrylate, trimethylolethane triacrylate, trimethylolpropane trimethacrylate, trimethylolethane trimethacrylate, tetramethylene glycol dimethacrylate, tri-ethylene glycol dimethacrylate, tetraethylene glycol diacrylate, pentaerythritol diacrylate, penta-erythritol triacrylate, pentaerythritol tetraacrylate, dipentaerythritol diacrylate, dipenta-erythritol triacrylate, dipentaerythritol tetraacrylate, dipentaerythritol pentaacrylate, dipenta-erythritol hexaacrylate, tripentaerythritol octaacrylate, pen-taerythritol dimethacrylate, penta-erythritol trimethacrylate, dipentaerythritol dimethacrylate, dipentaerythritol tetrameth-acrylate, tripentaerythritol octamethacrylate, pen-taerythritol diitaconate, dipentaerythritol trisitaconate, dipentaerythritol pentaitaconate, dipentaerythritol hexaitaconate, ethylene glycol diacrylate, 1,3-butanediol diacrylate, 1,3-butanediol dimethacrylate, 1,4-butanediol diitaconate, sorbitol triacrylate, sorbitol tetraacrylate, pentaerythritol-modified triacrylate, sorbitol tetramethacrylate, sorbitol pentaacrylate, sorbitol hexaacrylate, oligoester acrylates and methacrylates, glycerol di- and tri-acrylate, 1,4-cyclohexane diacrylate, bisacrylates and bismethacrylates of polyethylene glycol having a molecular weight of from 200 to 1500, and mixtures thereof.

Suitable unsaturated, free-radically polymerisable compounds are also the amides of the same or different unsaturated carboxylic acids and aromatic, cycloaliphatic and aliphatic polyamines having preferably from 2 to 6, especially from 2 to 4, amino groups. Examples of such polyamines are ethylenediamine, 1,2- or 1,3-propylenediamine, 1,2-, 1,3- or 1,4-butylenediamine, 1,5-pentylenediamine, 1,6-hexylenediamine, octylenediamine, dodecyl-enediamine, 1,4-diaminocyclohexane, isophoronediamine, phenylenediamine, bisphenylenediamine, di-β-aminoethyl ether, diethylenetriamine, triethylenetetraamine and di(β-aminoethoxy)- or di-(β-aminopropoxy)-ethane. Further suitable polyamines are polymers and copolymers which may have additional amino groups in the side chain and oligoamides having amino terminal groups. Examples of such unsaturated amides are: methylene bisacrylamide, 1,6-hexamethylene bisacrylamide, bis(methacrylamidopropoxy) ethane, β-methacrylamidoethyl methacrylate and N-[(β-hydroxyethoxy)ethyl]-acrylamide.

Suitable unsaturated polyesters and polyamides are derived, for example, from maleic acid and diols or diamines. The maleic acid may have been partially replaced by other dicarboxylic acids. They can be used together with ethylenically unsaturated comonomers, for example styrene. The polyesters and polyamides can also be derived from dicarboxylic acids and ethylenically unsaturated diols or diamines, especially from those having longer chains of, for example, from 6 to 20 carbon atoms. Examples of polyurethanes are those composed of saturated or unsaturated diisocyanates and saturated or unsaturated diols.

Polybutadiene and polyisoprene and copolymers thereof are known. Suitable comonomers include, for example, olefins, such as ethylene, propene, butene, hexene, (meth) acrylates, acrylonitrile, styrene and vinyl chloride. Polymers having (meth)acrylate groups in the side chain are also known. They may be, for example, reaction products of novolak-based epoxy resins with (meth)acrylic acid; homo- or co-polymers of vinyl alcohol or hydroxyalkyl derivatives thereof that have been esterified with (meth)acrylic acid; or homo- and co-polymers of (meth)acrylates that have been esterified with hydroxyalkyl (meth)acrylates.

It is also possible to use compounds that can be crosslinked equally both free-radically and cationically. Such compounds contain, for example, both a vinyl group and a cycloaliphatic epoxy group. Examples thereof are described in JP-A-2-289611 and U.S. Pat. No. 6,048,953.

Mixtures of two or more such free-radically polymerisable materials can also be used.

Binders may also be added to the compositions according to the invention, this being especially advantageous when the photopolymerisable compounds are liquid or viscous substances. The amount of binder may be, for example, from 5 to 95% by weight, preferably from 10 to 90% by weight and especially from 40 to 90% by weight, based on total solids. The binder will be selected according to the field of use and the properties required therefor, such as developability in aqueous and organic solvent systems, adhesion to substrates and sensitivity to oxygen.

Suitable binders are, for example, polymers having a molecular weight of approximately from 2,000 to 2,000,000, preferably from 5,000 to 1,000,000. Examples thereof are: homo- and copolymers of acrylates and methacrylates, for example copolymers of methyl methacrylate/ethyl acrylate/methacrylic acid, poly(methacrylic acid alkyl esters), poly (acrylic acid alkyl esters); phenolic resins, cellulose derivatives, such as cellulose esters and ethers, for example cellulose acetate, cellulose acetate butyrate, methyl cellulose, ethyl cellulose; polyvinyl butyral, polyvinylformal, polyolefins, cyclised rubber, polyethers, such as poly-ethylene oxide, polypropylene oxide, polytetrahydrofuran; polystyrene, polycarbonate, poly-urethane, chlorinated polyolefins, polyvinyl chloride, copolymers of vinyl chloride/vinylidene chloride, copolymers of vinylidene chloride with acrylonitrile, methyl methacrylate and vinyl acetate, polyvinyl acetate, copoly(ethylene/vinyl acetate), polymers such as polycaprolactam and poly (hexamethyleneadipamide), polyesters such as poly (ethylene glycol terephthalate) and poly(hexamethylene glycol succinate); and polyamides.

The resins mentioned below under (C1) may also be used as free-radically curable component. Of particular interest are, for example, unsaturated acrylates having reactive functional groups. The reactive functional group may be selected, for example, from a hydroxyl, thiol, isocyanate, epoxy, anhydride, carboxyl, amino or blocked amino group. Examples of OH-group-containing unsaturated acrylates are hydroxyethyl and hydroxybutyl acrylates and also glycidyl acrylates.

The unsaturated compounds may also be used in admixture with non-photopolymerisable film-forming components. These may be, for example, polymers that can be dried physically or solutions thereof in organic solvents, such as nitrocellulose or cellulose acetobutyrate. They may alternatively be chemically or thermally curable resins, such as polyisocyanates, polyepoxides or melamine resins. Drying oils, such as linseed oil, linseed-oil-modified alkyd resins, tung oil and soybean oil, can also be present. The concomitant use of thermally curable resins is important for use in so-called hybrid systems which are photopolymerised in a first step and crosslinked by thermal aftertreatment in a second step.

Thus, the radiation-curable compositions of the present invention may also comprise:

(A1) compounds having one or more free-radically polymerisable double bonds that additionally contain at least one further functional group that is reactive in addition and/or condensation reactions (examples are given above), (A2) compounds having one or more free-radically polymerisable double bonds that additionally contain at least one further functional group that is reactive in addition and/or condensation reactions, the additional functional group being complementary to or reactive towards the additional functional group of component (A1), (A3) at least one monomeric, oligomeric and/or polymeric compound having at least one functional group that is reactive in addition and/or condensation reactions towards the functional groups of component (A1) or (A2) that are present in addition to the free-radically polymerisable double bonds.

Component (A2) in each case carries the groups complementary to or reactive towards component (A1). Different types of functional groups may also be present in a component. Component (A3) provides a component that contains further functional groups that are reactive in addition and/or condensation reactions and that are able to react with the functional groups of (A1) or (A2) that are present in addition to the free-radically polymerisable double bonds. Component (A3) contains no free-radically polymerisable double bonds.

Examples of such combinations (A1), (A2), (A3) can be found in WO 99755785.

Examples of suitable functional groups are hydroxyl, isocyanate, epoxy, anhydride, carboxyl and blocked amino groups. Examples have been described above.

Constituents of the thermally curable component (C) are, for example, thermally curable lacquer or coating system constituents customary in the art. Component (C) accordingly may consist of a large number of constituents.

Examples of component (C) include oligomers and/or polymers derived from α,β-unsaturated acids and derivatives thereof, for example polyacrylates and polymethacrylates, polymethyl methacrylates impact-resistant-modified with butyl acrylate, polyacrylamides and polyacrylonitriles. Further examples of component (C) are urethanes, polyurethanes derived on the one hand from polyethers, polyesters and polyacrylates having free hydroxyl groups and on the other hand from aliphatic or aromatic polyisocyanates, and educts thereof. Component (C) accordingly also includes, for example, crosslinkable acrylic resins derived from substituted acrylic acid esters, for example epoxy acrylates, urethane acrylates and polyester acrylates. Alkyd resins, polyester resins and acrylate resins and modifications thereof that are crosslinked with melamine resins, urea resins, isocyanates, isocyanurates, polyisocyanates, polyisocyanurates and epoxy resins, may also be a constituent of component (C).

Component (C) is, for example, generally a film-forming binder based on a thermoplastic or thermocurable resin, especially on a thermocurable resin. Examples thereof are alkyd, acrylic, polyester, phenolic, melamine, epoxy and polyurethane resins and mixtures thereof. Examples thereof can be found, for example, in Ullmann's Encyclopedia of Industrial Chemistry, 5th Ed., Vol. A18, pp. 368–426, VCH, Weinheim 1991.

Component (C) may also be a cold-curable or hot-curable binder, in which case the addition of a curing catalyst may be advantageous. Suitable catalysts that accelerate the full cure of the binder can be found, for example, in Ullmann's Encyclopedia of Industrial Chemistry, Vol. A18, page 469, VCH Verlagsgesellschaft, Weinheim 1991.

Specific examples of binders suitable as component (C) are:

1. surface-coatings based on cold- or hot-crosslinkable alkyd, acrylate, polyester, epoxy or melamine resins or mixtures of such resins, optionally with the addition of a curing catalyst;
2. two-component polyurethane surface-coatings based on hydroxyl-group-containing acrylate, polyester or polyether resins and aliphatic or aromatic isocyanates, isocyanurates or polyisocyanates;
3. one-component polyurethane surface-coatings based on blocked isocyanates, isocyanurates or polyisocyanates, which are de-blocked during heating; it is also possible to add melamine resins as appropriate;
4. one-component polyurethane surface-coatings based on aliphatic or aromatic urethanes or polyurethanes and hydroxyl-group-containing acrylate, polyester or polyether resins;
5. one-component polyurethane surface-coatings based on aliphatic or aromatic urethane acrylates or polyurethane acrylates having free amine groups in the urethane structure and melamine resins or polyether resins, optionally with the addition of a curing catalyst;
6. two-component surface-coatings based on (poly) ketimines and aliphatic or aromatic isocyanates, isocyanurates or polyisocyanates;
7. two-component surface-coatings based on (poly) ketimines and an unsaturated acrylate resin or a polyacetoacetate resin or a methacrylamidoglycolate methyl ester;
8. two-component surface-coatings based on carboxyl- or amino-group-containing polyacrylates and polyepoxides;
9. two-component surface-coatings based on anhydride-group-containing acrylate resins and a polyhydroxy or polyamino component;
10. two-component surface-coatings based on acrylate-containing anhydrides and polyepoxides;
11. two-component surface-coatings based on (poly) oxazolines and anhydride-group-containing acrylate resins or unsaturated acrylate resins or aliphatic or aromatic isocyanates, isocyanurates or polyisocyanates;
12. two-component surface-coatings based on unsaturated polyacrylates and polymalonates;
13. thermoplastic polyacrylate surface-coatings based on thermoplastic acrylate resins or extrinsically crosslinking acrylate resins in combination with etherified melamine resins;
14. surface-coating systems based on urethane (meth) acrylate having (meth)acryloyl groups and free isocyanate groups and on one or more compounds that react with iso-cyanates, for example free or esterified polyols. Such systems have been published, for example, in EP 928800.

Blocked isocyanates that can also be used as component (C) are described, for example, in Organischer Metallschutz: Entwicklung und Anwendung von Beschichtungsstoffen, pages 159–160, Vincentz Verlag, Hanover (1993). These are compounds in which the highly reactive NCO group is "blocked" by reaction with specific radicals, for example a primary alcohol, phenol, acetic acid ethyl ester, F-caprolactam, phthalimide, imidazole, oxime or amine. The blocked isocyanate is stable in liquid systems and also in the presence of hydroxy groups. Upon heating, the blocking group (protecting group) is removed again and the NCO group is freed.

1-Component (1C) and 2-component (2C) systems may be used as component (C). Examples of such systems are described in Ullmann's Encyclopedia of Industrial Chemistry, Vol. A18, Paints and Coatings, pages 404–407, VCH Verlagsgesellschaft mbH, Weinheim (1991).

It is possible to optimise the composition by specific adaptation, for example by varying the binder/crosslinking agent ratios. Such measures will be known to the person skilled in the art and are customary in coating technology.

In the curing process according to the invention, component (C) is preferably a mixture based on acrylate/melamine (and melamine derivatives), 2-component polyurethane, 1-component polyurethane, 2-component epoxy/carboxy or 1-component epoxy/carboxy. Mixtures of such systems are also possible, for example the addition of melamine (or derivatives thereof) to 1-component polyurethanes.

Component (C) is preferably a binder based on a polyacrylate with melamine or on a melamine derivative or a system based on a polyacrylate and/or polyester polyol with an unblocked polyisocyanate or polyisocyanurate.

Component (C) may also comprise monomeric and/or oligomeric compounds having ethylenically unsaturated bonds (prepolymers) that additionally contain at least one or more OH, $NH_2$, COOH, epoxy or NCO group(s) (=C1) that are capable of reaction with the binder and/or the crosslinking agent constituent of component (C). After application and thermal curing, the ethylenically unsaturated bonds are converted to a crosslinked, high molecular weight form by irradiation with UV light. Examples of such components (C) are described, for example, in the above-mentioned publication, Ullmann's Encyclopedia of Industrial Chemistry, 5th Ed., Vol. A18, pages 451–453, or by S. Urano, K. Aoki, N. Tsuboniva and R. Mizuguchi in Progress in Organic Coatings, 20 (1992), 471–486, or by H. Terashima and O. Isozaki in JOCCA 1992 (6), 222.

(C1) may, for example, also be an OH-group-containing unsaturated acrylate, for example hydroxyethyl or hydroxybutyl acrylate or a glycidyl acrylate. Component (Cl) may be of any desired structure (for example it may contain units of polyester, polyacrylate, polyether, etc.), provided that it contains an ethylenically unsaturated double bond and additionally free OH, COOH, $NH_2$, epoxy or NCO groups.

(C1) may, for example, also be obtained by reacting an epoxy-functional oligomer with acrylic acid or methacrylic acid. A typical example of an OH-functional oligomer having vinylic double bonds is

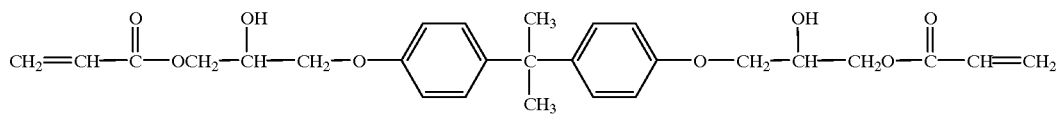

obtained by reaction

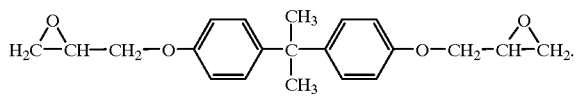

of CH$_2$=CHCOOH with

Another possible method of obtaining component (C1) is, for example, the reaction of an oligomer that contains only one epoxy group and has a free OH group at another position in the molecule.

The quantity ratio of the free-radically radiation-curable-polymerisable components to the thermally polymerisable component (C) in the UV- and thermally-crosslinkable formulations is not critical. "Dual-cure" systems are known to the person skilled in the art, who will therefore be familiar with the optimum mixing ratios of the free-radically- and thermally-crosslinkable components according to the intended use. For example, the ratio can be in the range from 5:95 to 95:5, from 20:80 to 80:20 or from 30:70 to 70:30, for example from 40:60 to 60:40.

Examples of "dual-cure" systems, that is to say systems comprising both radiation-curable and thermally curable components, can be found inter alia in U.S. Pat. No. 5,922, 473, columns 6 to 10.

The formulations according to the invention can further comprise as component (a1) non-aqueous coating compositions based on an oxidatively drying alkyd resin which contains at least one, preferably two or more, functional group(s) capable of undergoing polymerisation or polycondensation reactions in the presence of an acid. Examples of such resins are vinyl-ether-functionalised alkyd resins, acetal-functionalised alkyd resins, and/or alkoxysilane-functionalised alkyd resins, as proposed, e.g., in WO 99/47617. Those modified alkyd resins may be used alone or in combination with other alkyd resins. At least some of the alkyd resin composition in the non-aqueous coating is oxidatively drying as a result of the incorporation of a large number of unsaturated, aliphatic compounds, at least some of which are polyunsaturated.

Formulations containing those modified alkyd resins as component (a1) may optionally contain, in addition to the photoinitiator (b), an oxidative dryer. Suitable oxidative dryers are, for example, metal siccatives. There may be mentioned as suitable siccatives, for example, the metal salts of (cyclo)aliphatic acids, such as octanoic acid and naphthenic acid, the metals to be used being, for example, cobalt, manganese, lead, zirconium, calcium, zinc and rare earth metals. Mixtures of siccatives may be used. Preference is given to metal salts of cobalt, zirconium and calcium, or mixtures thereof. The siccatives (calculated as metal) are usually used in an amount of from 0.001 to 3% by weight.

Under certain conditions it may also be advantageous, when using the modified alkyd resins as component (a1), to use one or more mono- or bis-acylphosphine oxide photoinitiators in addition to the diaryliodonium salt of formula (I). Suitable monoacyl- or bisacyl-phosphine oxide photoinitiators include, for example, monoacylphosphine oxides such as (2,4,6-trimethylbenzoyl)-diphenylphosphine oxide (Lucirin® TPO) or (2,4,6-trimethylbenzoyl-phenyl-ethoxy-phosphine oxide, or bisacylphosphine oxide photoinitiators such as bis(2,6-dimethoxybenzoyl)-2,4,4-trimethylpentyl-phosphine oxide, bis(2,6-dimethoxybenzoyl)-2,2,4-trimethyl-pentyl-phosphine oxide, bis(2,4,6-trimethylbenzoyl)-(2,4-dipentyloxyphenyl)-phosphine oxide and bis(2,4,6-trimethylbenzoyl)phenyl-phosphine oxide. Those monoacyl- or bisacyl-phosphine oxides are advantageously used in an amount of from 0.5 to 5%. When component (a1) contains modified alkyd resins, in addition to the photoinitiator (b) it is also possible to use an oxidative dryer and suitable monoacyl- or bisacyl-phosphine oxide photoinitiators.

The alkyd resins used as component (a1) contain a large number of unsaturated, aliphatic compounds, at least some of which are polyunsaturated. The unsaturated aliphatic compounds preferably used for the preparation of those alkyd resins are unsaturated aliphatic monocarboxylic acids, especially polyunsaturated aliphatic monocarboxylic acids.

Examples of mono-unsaturated fatty acids are myristoleic acid, palmitic acid, oleic acid, gadoleic acid, erucic acid and ricinoleic acid. Preferably fatty acids containing conjugated double bonds, such as dehydrogenated castor oil fatty acid and/or tung oil fatty acid, are used. Other suitable mono-carboxylic acids include tetrahydrobenzoic acid and hydrogenated or non-hydrogenated abietic acid or the isomers thereof. If desired, the monocarboxylic acid in question may be used wholly or in part in the form of a triglyceride, e.g. as vegetable oil, in the preparation of the alkyd resin. If desired, mixtures of two or more such mono-carboxylic acids or triglycerides may be used, optionally in the presence of one or more saturated, (cyclo)aliphatic or aromatic mono-carboxylic acids, e.g. pivalic acid, 2-ethyl-hexanoic acid, lauric acid, palmitic acid, stearic acid, 4-tert-butyl-benzoic acid, cyclo-pentanecarboxylic acid, naphthenic acid, cyclo-hexanecarboxylic acid, 2,4-dimethylbenzoic acid, 2-methylbenzoic acid and benzoic acid.

If desired, polycarboxylic acids may also be incorporated into the alkyd resin, such as phthalic acid, isophthalic acid, terephthalic acid, 5-tert-butylisophthalic acid, trimellitic acid, pyromellitic acid, succinic acid, adipic acid, 2,2,4-trimethyladipic acid, azelaic acid, sebacic acid, dimerised fatty acids, cyclopentane-1,2-dicarboxylic acid, cyclohexane-1,2-dicarboxylic acid, 4-methylcyclohexane-1,2-dicarboxylic acid, tetrahydrophthalic acid, endomethylenecyclohexane-1,2-dicarboxylic acid, butane-1,2,3,4-tetracarboxylic acid, endoisopropylidenecyclohexane-1,2-dicarboxylic acid, cyclohexane-1,2,4,5-tetracarboxylic acid and butane1,2,3,4-tetracarboxylic acid. If desired, the carboxylic acid in question may be used as an anhydride or in the form of an ester, for example an ester of an alcohol having from 1 to 4 carbon atoms.

In addition, the alkyd resin can be composed of di- or poly-valent hydroxyl compounds.

Examples of suitable divalent hydroxyl compounds are ethylene glycol, 1,3-propanediol, 1,6-hexanediol, 1,12- dodecanediol, 3-methyl-1,5-pentanediol, 2,2,4-trimethyl-1, 6-hexane-diol, 2,2-dimethyl-1,3-propanediol and 2-methyl-2-cyclohexyl-1,3-propanediol. Examples of suitable triols are glycerol, trimethylolethane and trimethylolpropane. Suitable polyols having more than 3 hydroxyl groups are pentaerythritol, sorbitol and etherified products of the compounds in question, such as ditrimethylolpropane and di-, tri- and tetra-pentaerythritol. Preferably, compounds having from 3 to 12 carbon atoms, e.g. glycerol, pentaerythritol and/or dipentaerythritol, are used.

The alkyd resins can be obtained by direct esterification of the constituents, with the option that some of those components may already have been converted into ester diols or polyester diols. The unsaturated fatty acids can also be used in the form of a drying oil, such as linseed oil, tuna fish oil, dehydrogenated castor oil, coconut oil and dehydrogenated coconut oil. The final alkyd resin is then obtained by transesterification with the other acids and diols added. The transesterification is advantageously carried out at a temperature in the range of from 115 to 250° C., optionally in the presence of solvents such as toluene and/or xylene. The reaction is advantageously carried out in the presence of a catalytic amount of a transesterification catalyst. Examples of suitable transesterification catalysts include acids, such as p-toluenesulfonic acid, basic compounds, such as an amine, or compounds such as calcium oxide, zinc oxide, tetraisopropyl orthotitanate, dibutyltin oxide and triphenylbenzylphosphonium chloride.

The vinyl ether, acetal and/or alkoxysilane compounds used as part of component (a1) preferably contain at least two vinyl ether, acetal and/or alkoxysilane groups and have a molecular weight of 150 or more. Those vinyl ether, acetal and/or alkoxysilane compounds can be obtained, for example, by the reaction of a commercially available vinyl ether, acetal and/or alkoxysilane compound containing a vinyl ether, acetal and/or alkoxysilane group and in addition a maximum of one functional amino, epoxy, thiol, isocyanate, acrylic, hydride or hydroxyl group, with a compound having at least two groups capable of reacting with an amino, epoxy, thiol, isocyanate, acrylic, hydride or hydroxyl group. As examples thereof there may be mentioned compounds having at least two epoxy, isocyanate, hydroxyl and/or ester groups or compounds having at least two ethylenically or ethynylenically unsaturated groups.

As component (a1), preference is given to a composition in which the vinyl ether, acetal and/or alkoxysilane compounds are covalently bonded to the alkyd resin by addition via a reactive group such as an amino, hydroxyl, thiol, hydride, epoxy and/or isocyanate group. For that purpose, the compounds must have at least one group capable of forming an adduct with the reactive groups present in the alkyd resin.

To incorporate vinyl ether groups into the alkyd resin, use is made of a vinyloxyalkyl compound, the alkyl group of which is substituted by a reactive group, such as a hydroxyl, amino, epoxy or isocyanate group, that is capable of forming an adduct with one or more of the reactive groups present in the alkyd resin.

As component (a1), preference is given to compositions in which the ratio of the number of oxidatively drying groups present in the alkyd resin to the number of groups that are reactive in the presence of an acid is in the range of from 1/10 to 15/1, especially from 1/3 to 5/1. Instead of a single modified alkyd resin, it is also possible to use a plurality of alkyd resins, with one alkyd resin being highly modified and the others being less modified or not modified at all.

Examples of vinyl ether compounds capable of being covalently bonded to the alkyd resin are ethylene glycol monovinyl ether, butanediol monovinyl ether, hexanediol monovinyl ether, triethylene glycol monovinyl ether, cyclohexanedimethanol monovinyl ether, 2-ethyl-hexanediol monovinyl ether, polytetrahydrofuran monovinyl ether, tetraethylene glycol monovinyl ether, trimethylolpropane divinyl ether and aminopropyl vinyl ether.

Adducts can be formed, for example, by reacting the vinyl ether compounds containing a hydroxyl group or amino group with an excess of a diisocyanate, followed by the reaction of that free-isocyanate-group-containing adduct with the free hydroxyl groups of the alkyd resin. Preferably, a process is used in which first the free hydroxyl groups of the alkyd resin react with an excess of a polyisocyanate, and then the free isocyanate groups react with an amino-group- or hydroxyl-group-containing vinyl ether compound. Instead of a diisocyanate, it is also possible to use a diester. Transesterification of the hydroxyl groups present in the alkyd resin with an excess of the diester, followed by transesterification or transamidation of the remaining ester groups with hydroxy-functional vinyl ether compounds or amino-functional vinyl ether compounds, respectively, yields vinyl-ether-functional alkyd resins. It is also possible to incorporate (meth)acrylate groups into the alkyd resin during preparation of the alkyd resin, by carrying out the preparation in the presence of a hydroxy-functional (meth) acrylate ester, such as hydroxyethyl methacrylate (HEMA), and then reacting the thus functionalised alkyd resin by means of a Michael reaction with a vinyl-ether-group-containing compound and a primary-amino-group-containing compound, followed by reaction with e.g. an isocyanate compound, in order to obtain a non-basic nitrogen atom.

An example of such a reaction is described, for example, in WO 99/47617. Esterification of ricinine fatty acid with dipentaerythritol, followed by transesterification of the free hydroxyl groups with diethyl malonate and 4-hydroxybutyl vinyl ether in a suitable ratio, yields a vinyl-ether-functional alkyd resin suitable for use as component (a1).

For the preparation of acetal-functional alkyd resins, use is generally made of dialkyl acetal functionalised with an amino group. Examples of suitable acetal compounds include 4-aminobutyraldehyde dimethyl acetal and 4-aminobutyraldehyde diethyl acetal. The alkyd resin is modified by the addition of the aminoacetal monomer to an alkyd resin functionalised with isocyanate groups, with ester groups of a low-boiling alcohol or with (meth)acrylate groups. The resulting dialkyl-acetal-modified alkyd resin can be incorporated into the coating composition having a high solids content and low viscosity. The preparation of acetal-functional alkyd resins can also be carried out by reacting hydroxyacetal with the carboxyl groups of the alkyd resin or by reacting a diisocyanate or diester compound with the hydroxyl groups of the alkyd resin.

An example of this preparative method is described in WO 99/47617, for example the esterification of a hydroxy-functional alkyd resin with diethyl malonate, followed by transamidation of the free ester group with 4-aminobutyraldehyde dimethyl acetal in a suitable ratio. The resulting acetal-modified alkyd resin is suitable as component (a1).

For the incorporation of alkoxysilane groups into the alkyd resin, use is made of a siloxane compound having one or more reactive group(s) which are subsequently reacted with one or more of the constituents making up the alkyd resin. These are, for example, alkoxy-silanes of the formula:

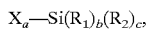

wherein $R_1$ is alkoxy or oxyalkylenealkoxy or, when X is hydrogen, $R_1$ is halogen, $R_2$ is an aliphatic, cycloaliphatic or aromatic group, and X is hydrogen or an alkyl group substituted by an amino, isocyanate, mercapto or epoxy group; a is from 1 to 3, b is from 1 to 3, c is from 0 to 2, and a+b+c=4.

$R_1$ is preferably an alkoxy group having from 1 to 4 carbon atoms in the alkoxy group, and $R_2$ is preferably a group having not more than 18 carbon atoms.

Examples of suitable siloxane compounds are 3-aminopropyl-triethoxysilane, polyglycolether-modified aminosilane, 3-aminopropyl-trimethoxysilane, 3-aminopropyltris-methoxy-ethoxyethoxysilane, 3-aminopropyl-methyl-diethoxysilane, N-2-aminoethyl-3-aminopropyl-trimethoxy-silane, N-2-aminoethyl-3-aminopropyl-methyldimethoxy-silane, N-methyl-3-aminopropyl-trimethoxysilane, 3-ureidopropyl-triethoxysilane, 3,4,5-dihydroimidazol-1-yl-propyltriethoxysilane, 3-methacryloxypropyl-trimethoxysilane, 3-glycidyloxypropyl-trimethoxysilane, 3-mercaptopropyl-trimethoxysilane and 3-mercaptopropyl-methyl-dimethoxysilane, triethoxysilane, diethoxymethylsilane, dimethoxymethylsilane, tri-methoxysilane, trichlorosilane, triiodosilane, tribromosilane, dichloromethylsilane and dibromomethylsilane.

The alkyd resin can be modified, for example, by the insertion of an amino-group-modified alkoxysilane into an alkyd resin modified with a polyisocyanate or a polyester of a low-boiling alcohol. Hydride-functional alkoxysilanes can be bonded directly to the alkyd, i.e. without modification with a binding molecule such as a diisocyanate or diester, by adding a compound containing a silylhydride group to an ethylenically unsaturated group in the alkyd resin. That addition is catalysed by a transition metal. In that process, use is preferably made of a halogenated silylhydride and, in order to terminate the addition reaction, conversion into an alkoxysilane compound with a low-boiling alcohol. The addition reaction is advantageously carried out in the absence of sterically hindering groups and proceeds in optimum manner when the ethylenically unsaturated groups are terminal groups, as is the case, for example, with esters of 10-undecenecarboxylic acid.

Examples of the preparation of alkoxysiloxane-modified alkyd resins are described in WO 99/47617. Esterification of a hydroxy-functional alkyd resin with diethyl malonate, followed by transamidation of the free ester group with 3-aminopropyltriethoxysilane in a suitable ratio yields an alkoxysilane-modified alkyd resin. Hydroxy-modified alkyd resin can also be reacted with an excess of isophorone diisocyanate, followed by reaction of the free isocyanate groups with 3-aminopropyltriethoxysilane. Both alkoxysiloxane-modified alkyd resins obtained by the processes described are suitable for use in component (a1).

When free-radically polymerisable components have been added to the formulation according to the invention, it may be advantageous to add also a suitable free-radical photoinitiator or a mixture of such photoinitiators, e.g. benzophenone and derivatives thereof, acetophenone and derivatives thereof, e.g. α-hydroxycyclohexylphenyl ketone or 2-hydroxy-2-methyl1-phenyl-propanone, 2-hydroxy-1-[3-[4-(2-hydroxy-2-methyl-propionyl)-phenyl]-1,1,3-trimethyl-indan-5-yl]-2-methyl-propan-1-one, α-hydroxy- or α-amino-acetophenone, such as, for example, (4-methylthiobenzoyl)-1-methyl-1-morpholino-ethane, (4-morpholino-benzoyl)-1-benzyl- 1-dimethylamino-propane, 4-aroyl-1,3-dioxolane, benzoin alkyl ethers and benzil ketal, such as, for example, benzil dimethyl ketal, phenyl glyoxalate and derivatives thereof, mono- or bis-acylphosphine oxide, such as, for example, (2,4,6-trimethyl-benzoyl)-phenyl-phosphine oxide, bis(2,6-dimethoxybenzoyl)-(2,4,4-trimethyl-pent-1-yl)phosphine oxide, bis(2,4,6-trimethylbenzoyl)-phenyl-phosphine oxide or bis(2,4,6-trimethylbenzoyl)-(2,4-dipentyloxyphenyl) phosphine oxide.

Other additional components can be, for example, hydroxy-functional components, such as alcohols, polyester polyols, polyether polyols, hydroxy-group-containing polyurethanes, castor oil, etc. Examples thereof include aliphatic and cycloaliphatic polyols, such as alkylene diols having preferably from 2 to 12 carbon atoms, e.g. ethylene glycol, 1,2- or 1,3-propanediol, 1,2-, 1,3- or 1,4-butanediol, pentanediol, hexanediol, octanediol, dodecanediol, diethylene glycol, triethylene glycol, polyethylene glycols having molecular weights of preferably from 200 to 1500, 1,3-cyclopentanediol, 1,2-, 1,3- or 1,4-cyclohexanediol, 1,4-di-hydroxymethylcyclohexane, glycerol, tris(β-hydroxy-ethyl) amine, trimethylolethane, tri-methylolpropane, pentaerythritol, dipentaerythritol and sorbitol. The polyols can be partially or fully esterified by one or by different unsaturated carboxylic acids, it being possible for the free hydroxyl groups in partial esters to have been modified, e.g. etherified, or esterified by other carboxylic acids. Examples of esters include: trimethylolpropane triacrylate, trimethylolethane triacrylate, trimethylolpropane trimethacrylate, trimethylolethane trimeth-acrylate, tetramethylene glycol dimethacrylate, triethylene glycol dimethacrylate, tetraethylene glycol diacrylate, pentaerythritol diacrylate, pentaerythritol triacrylate, pentaerythritol tetraacrylate, dipentaerythritol diacrylate, dipentaerythritol triacrylate, dipentaerythritol tetraacrylate, dipentaerythritol pentaacrylate, dipentaerythritol hexaacrylate, tripentaerythritol octaacrylate, pentaerythritol dimethacrylate, pentaerythritol trimethacrylate, dipenta-erythritol dimethacrylate, dipentaerythritol tetramethacrylate, tripentaerythritol octamethacrylate, pentaerythritol diitaconate, dipentaerythritol trisitaconate, dipentaerythritol pentaitaconate, dipentaerythritol hexaitaconate, ethylene glycol diacrylate, 1,3-butanediol diacrylate, 1,3-butanediol dimethacrylate, 1,4-butanediol diitaconate, sorbitol triacrylate, sorbitol tetraacrylate, pentaerythritol-modified triacrylate, sorbitol tetramethacrylate, sorbitol pentaacrylate, sorbitol hexaacrylate, oligoester acrylates and methacrylates, glycerol di- and tri-acrylate, 1,4-cyclohexane diacrylate, bisacrylates and bismethacrylates of polyethylene glycol having a molecular weight of from 200 to 1500, or mixtures thereof.

The iodonium salt compounds of formula I can also be used, for example, as photoactivatable hardeners for siloxane-group-containing resins. Those resins can, for example, either undergo self-condensation by way of acid-catalysed hydrolysis or can be crosslinked with a second resin component, such as, for example, a polyfunctional alcohol, a hydroxy group-containing acrylic or polyester resin, a partially hydrolysed polyvinylacetal or a polyvinyl alcohol. That type of polycondensation of polysiloxanes is described, for example, in J. J. Lebrun, H. Pode, Comprehensive Polymer Science Vol. 5, page 593, Pergamon Press, Oxford, 1989.

Examples of compounds whose solubility increases in a developer under the action of acid (component (a2)) include oligomers, polymers and copolymers that can be obtained by copolymerisation of, for example, the following monomers: non-cyclic or cyclic secondary and tertiary alkyl (meth) acrylates, such as tert-butyl acrylate, tert-butyl methacrylate, 3-oxo-cyclohexyl (meth)acrylate, tetrahydropyranyl (meth) acrylate, 2-methyl-2-adamantyl (meth)acrylate, cyclohexyl (meth)acrylate, norbornyl (meth)acrylate, isobornyl methacrylate, 5-norbornene-2-tert-butyl ester, 8-ethyl-8-tricyclodecanyl (meth)acrylate, (2-tetrahydro-pyranyl) oxynorbornylalcohol acrylates, (2-tetrahydropyranyl) oxymethyltricyclododecanemethanol methacrylates, trimethylsilylmethyl (meth)acrylates, (2-tetrahydropyranyl) oxy-norbornylalcohol acrylates, (2-tetrahydropyranyl) oxymethyltricyclododecanemethanol methacrylates, trimethylsilylmethyl (meth)acrylate, o-/m-/p-(3-oxocyclohexyloxy)styrene, o-/m-/p-(1-methyl-1-phenylethoxy)styrene, o-/m-/p-tetrahydropyranyloxystyrene, o-/m-/p-adamantyloxystyrene, o-/m-/p-cyclohexyloxystyrene, o-/m-/p-norbornyloxystyrene, non-cyclic or cyclic alkoxycarbonylstyrenes, such as o-/m-/p-tert-butoxycarbonylstyrene, o-/m-/p-(3-oxocyclohexyloxycarbonyl)styrene, o-/m-/p-(1-methyl-1-phenylethoxycarbonyl)styrene, o-/m-/p-tetrahydropyranyloxycarbonylstyrene, o-/m-/p-adamantyloxycarbonylstyrene, o-/m-/p-cyclohexyloxycarbonylstyrene, o-/m-/p-norbornyloxycarbonylstyrene, non-cyclic or cyclic alkoxycarbonyloxystyrenes, such as o-/m-/p-tert-butoxycarbonyloxystyrene, o-/m-/p-(3-oxocyclohexyloxycarbonyloxy)styrene, o-/m-/p-(1-methyl-1-phenylethoxycarbonyloxy)-styrene, o-/m-/p-tetrahydropyranyloxycarbonyloxystyrene, o-/m-/p-adamantyloxycarbonyloxystyrene, o-/m-/p-cyclohexyloxycarbonyloxystyrene, o-/m-/p-norbornyloxycarbonyloxy-styrene, non-cyclic or cyclic alkoxycarbonylalkoxystyrenes, such as o-/m-/p-butoxycarbonylmethoxystyrene, p-tert-butoxycarbonylmethoxystyrene, o-/m-/p-(3-oxocyclohexyloxycarbonylmethoxy)styrene, o-/m-/p-(1-methyl-1-phenylethoxycarbonylmethoxy)styrene, o-/m-/p-tetrahydropyranyloxycarbonylmethoxystyrene, o-/m-/p-adamantyloxycarbonylmethoxy-styrene, o-/m-/p-cyclohexyloxycarbonylmethoxystyrene, o-/m-/p-norbornyloxycarbonyl-methoxystyrene, trimethylsiloxystyrene, dimethyl(butyl)siloxystyrene, unsaturated alkyl acetates, such as isopropenyl acetate and derivatives thereof, 5-norbornenyl-2-tert-butyl ester; also monomers that carry acid-labile groups having low activation energy, such as, for example, p- or m-(1-methoxy-1-methylethoxy)styrene, p- or m-(1-methoxy-1-methylethoxy)-methylstyrene, p- or m-(1-methoxy-1-methylpropoxy)styrene, p- or m-(1-methoxy-1-methylpropoxy)methylstyrene, p- or m-(1-methoxyethoxy) styrene, p- or m-(1-methoxyethoxy)-methylstyrene, p- or m-(1-ethoxy-1-methylethoxy)styrenes, p- or m-(1-ethoxy-1-methylethoxy)methylstyrene, p- or m-(1-ethoxy-1-methylpropoxy)styrene, p- or m-(1-ethoxy-1-methylpropoxy)methylstyrene, p- or m-(1-ethoxyethoxy) styrene, p- or m-(1-ethoxyethoxy)-methylstyrene, p-(1-ethoxyphenylethoxy)styrene, p- or m-(1-n-propoxy-1-methylethoxy)-styrene, p- or m-(1-n-propoxy-1-methylethoxy)methylstyrene, p- or m-(1-n-propoxyethoxy)-styrene, p- or m-(1-n-propoxyethoxy)methylstyrene, p- or m-(1-isopropoxy-1-methylethoxy)-styrene, p- or m-(1-isopropoxy-1-methylethoxy)methylstyrene, p- or m-(1-isopropoxyethoxy)-styrene, p- or m-(1-isopropoxyethoxy) methylstyrene, p- or m-(1-isopropoxy-1-methyl-propoxy) styrene, p- or m-(1-isopropoxy-1-methylpropoxy)-methylstyrene, p- or m-(1-iso-propoxypropoxy)styrene, p- or m-(1-isopropoxypropoxy)-methylstyrene, p- or m-(1-n-butoxy-1-methylethoxy)styrene, p- or m-(1-n-butoxyethoxy)styrene, p- or m-(1-isobutoxy-1-methyl-ethoxy)styrene, p- or m-(1-tert-butoxy-1-methylethoxy) styrene, p- or m-(1-n-pentyloxy-1-methylethoxy)styrene, p- or m-(1-isoamyloxy-1-methylethoxy)styrene , p- or m-(1-n-hexyloxy-1-methylethoxy)styrene, p- or m-(1-cyclohexyloxy-1-methylethoxy)styrene, p- or m-(1-trimethylsilyloxy-1-methylethoxy)styrene, p- or m-(1-trimethylsilyloxy-1-methylethoxy)-methylstyrene, p- or m-(1-benzyloxy-1-methylethoxy)styrene, p- or m-(1-benzyloxy-1-methylethoxy)methylstyrene, p- or m-(1-methoxy-1-methylethoxy)styrene, p- or m-(1-methoxy-1-methylethoxy)-methylstyrene, p- or m-(1-trimethylsilyloxy-1-methylethoxy)-styrene, p- or m-(1-trimethylsilyloxy-1-methylethoxy)methylstyrene. Further examples of polymers having alkoxyalkyl ester acid-labile groups can be found in U.S. Pat. No. 5,225,316 and EP 829766. Examples of polymers having acetal protecting groups are described, for example, in U.S. Pat. No. 5,670,299, EP 780 732, U.S. Pat. No. 5,627,006, U.S. Pat. No. 5,558,976, U.S. Pat. No. 5,558,971, U. 5,468,589, EP 704762, EP 762206, EP 342498, EP 553737 and in ACS Symp. Ser. 614, Microelectronics Technology, pp. 35–55 (1995), J. Photopolymer Sci. Technol. Vol. 10, No. 4 (1997), pp. 571–578, J. Photopolymer Sci. Technol. Vol. 12, no. 4 (1999) pp. 591–599 and in "Proceedings of SPIE", Advances in Resist Technology and Processing XVII, Vol. 3999, Part One, pp. 579–590. Feb. 28–Mar. 1, 2000. The polymers suitable in the composition according to the invention are not, however, limited thereto.

The monomers having an acid-labile group can, where appropriate, also be co-polymerised with other free-radically polymerisable monomers that do not carry acid-labile groups, such as, for example, styrene, acrylonitrile, methyl (meth)acrylate, (meth)acrylic acid, 4-hydroxystyrene 4-acetoxystyrene, 4-methoxystyrene, 4-vinylcyclohexanol, norbornene, ethylnorbornene and maleic acid anhydride, in order to establish specific solubility properties and adhesive properties. Alternatively, the acid-labile groups can be introduced only subsequently in a polymer-analogous reaction. It is also known to the person skilled in the art that the prepolymer can be modified in targeted manner before such a polymer-analogous reaction, for example by partial hydrogenation, partial alkylation, partial acetylation. That is to say, that the polymer having acid-labile groups does not, in every case, have to be synthesised from monomers by copolymerisation.

It is also possible to introduce acid-labile crosslinking, as described, for example, in H. T. Schacht, P. Falcigno, N. Muenzel, R. Schulz and A. Medina, ACS Symp. Ser. 706 (Micro- and Nanopatterning Polymers), pp. 78–94, 1997; H. T. Schacht, N. Muenzel, P. Falcigno, H. Holzwarth and J. Schneider, J. Photopolymer Science and Technology, Vol. 9, (1996), 573–586. Such acid-crosslinked systems are preferred in resist applications from the standpoint of heat stability. Such acid-labile crosslinking can also be obtained by the reaction of phenol-group-containing polymers, such as, for example, 4-hydroxystyrene co-polymers, with di- and poly-functional vinyl ethers.

Other examples of component (a2) that increase their solubility in an alkaline developer upon reaction with acid are monomeric compounds, such as, for example, carboxylic acids and phenol-group-containing compounds, in which the carboxylic acid group or phenolic OH group, respectively, has been blocked by acid-labile protecting groups. Such acid-labile blocking can be effected, for example, by conversion of the carboxyl group into a tert-butyl ester group, a 2-methyl-2-adamantyl ester group, an 8-ethyl-8-tricyclodecanyl ester group, a tetrahydropyranyl ester group or some other acid-cleavable ester group. Phenolic OH groups can be blocked according to known processes by conversion, e.g. into acid-cleavable tert-butylcarbonate groups, silyl ethers, acetal groups and ketal groups.

The invention relates also to a radiation-sensitive composition wherein component (a2) is at least one compound selected from the group of cycloaliphatic copolymers, 4-hydroxy-phenyl-group-containing copolymers, maleic acid anhydride-containing copolymers and acrylic acid-, acrylic acid ester- and methacrylic acid ester-containing copolymers, with the proviso that those copolymers carry functional groups that increase the solubility of the polymer in an alkaline developer after reaction with an acid.

In the compositions according to the invention, the photoinitiator (b) is advantageously used in an amount of from 0.05% to 15%, e.g. from 0.5% to 10%, preferably from 0.1% to 5%, based on the composition.

The compositions according to the invention can be used in numerous applications, for example in cationically radiation-curable printing inks, in cationically radiation-curable coating compounds which may or may not be pigmented, in cationically radiation-curable adhesives, coatings and mouldings, including glass fibre-reinforced and carbon fibre-reinforced composites and inner and outer layers of printed circuit boards.

The compositions according to the invention include also adhesives, as used, for example, for adhesive bonding (DVD bonding) in the manufacture of digital versatile disks (DVD) and as described, for example, in: WO 99/66506, WO 99/63017, JP 11241055 A2 Heisei, JP 11181391 A2 Heisei, WO 98/31765, and also as radiation-curable laminating adhesives for flexible packaging (see, e.g., U.S. Pat. No. 5328940), optical adhesives (e.g. German Patent Application DD 225985) and pressure-sensitive adhesives (e.g. U.S. Pat. No. 4,988,741 and EP 115870).

The compositions according to the invention are advantageously used where there is a need for hard coatings, adhesive bonds or photopolymerised dimensionally stable three-dimensional mouldings (e.g. for rapid prototyping) having good adhesion to paper, glass, metal, silicon, polycarbonate, acrylate polymers and other polymer substrates, and that exhibit only slight shrinkage during curing.

Preference is also given to a composition as described above that comprises in addition to components (a1) or (a2) and (b), additional additives (c) and/or sensitiser compounds (d) and optionally further photoinitiators (e).

The photopolymerisable mixtures can comprise various additives (c) in addition to the photoinitiator. Examples thereof include thermal inhibitors, light stabilisers, optical brighteners, fillers and pigments, as well as white and coloured pigments, dyes, antistatics, adhesion promoters, wetting agents, flow auxiliaries, lubricants, waxes, anti-adhesive agents, dispersants, emulsifiers, anti-oxidants, fillers, e.g. talcum, gypsum, silicic acid, rutile, carbon black, zinc oxide, iron oxides, reaction accelerators, thickeners, matting agents, antifoams, and other adjuvants customary, for example, in lacquer and coating technology.

The formulations can also comprise dyes and/or white or coloured pigments as additional additives (c). Depending upon the intended use, it is possible to use both inorganic and organic pigments. Such additives are known to the person skilled in the art; some examples thereof are titanium dioxide pigments, for example of the rutile or anatase type, carbon black, zinc oxide, such as zinc white, iron oxides, such as iron oxide yellow, iron oxide red, chromium yellow, chromium green, nickel titanium yellow, ultramarine blue, cobalt blue, bismuth vanadate, cadmium yellow and cadmium red. Examples of organic pigments are mono- or bis-azo pigments, and metal complexes thereof, phthalocyanine pigments, polycyclic pigments, such as, for example, perylene, anthraquinone, thioindigo, quinacridone and triphenylmethane pigments, and diketo-pyrrolo-pyrrole, isoindolinone, e.g. tetrachloro-isoindolinone, isoindoline, dioxazine, benzimidazolone and quinophthalone pigments.

The pigments can be used individually or in admixture in the formulations. Depending upon the intended use, the pigments are added to the formulations in amounts customary in the art, for example in an amount of from 1 to 60% by weight, or from 10 to 30% by weight, based on the total weight.

The formulations may, for example, also comprise organic dyes of a wide variety of classes. Examples thereof include azo dyes, methine dyes, anthraquinone dyes and metal complex dyes. Customary concentrations are, for example, from 0.1 to 20%, especially from 1 to 5%, based on the total weight.

The pigments, latent pigments or dyes or differently coloured precursors of such pigments and dyes that are added may be so selected that they undergo a colour change in the presence of the acid formed from the iodonium salt as a result of irradiation. Such compositions then show, by the colour change, that they have been irradiated and can be used, for example, as irradiation dose indicators, e.g. for UV radiation, electron beams, X-rays, etc.

The choice of additives will depend upon the field of use in question and upon the properties desired for that field. The additives (c) described above are customary in the art and are accordingly used in amounts customary in the art.

Acceleration of the photopolymerisation can also be effected by adding as further additives (d) photosensitisers that shift or broaden the spectral sensitivity. These are especially aromatic carbonyl compounds, such as, for example, benzophenone, thioxanthone, and especially also isopropylthioxanthone, phenothiazine derivatives, anthraquinone and 3-acylcoumarin derivatives, terphenyls, styryl ketones, and 3-(aroylmethylene)-thiazolines, camphorquinone, and also eosin, rhodamine and erythrosin dyes, and anthracene derivatives, such as, for example, 9-methylanthracene, 9,10-dimethylanthracene, 9,10-diethoxyanthracene, 9-methoxyanthracene, 9-anthracenemethanol, especially 9,10-dimethoxy-2-ethyl-anthracene and 9,10-diethoxyanthracene. Further suitable photosensitisers are mentioned, for example, in WO 9847046.

Subject of the invention also are radiation-sensitive compositions as described above, additionally to components (a1) or (a2) and (b) comprising at least one sensitizer compound (d), in particular benzophenone, thioxanthone, anthracene or derivatives thereof.

It is also possible to use electron donor compounds, such as, for example, alkyl- and arylamine donor compounds, in the composition. Such compounds are, for example, 4-dimethylaminobenzoic acid, ethyl 4-dimethylaminobenzoate, 3-dimethylaminobenzoic acid, 4-dimethylaminobenzoin, 4-dimethylaminobenzaldehyde, 4-dimethylaminobenzonitrile and 1,2,4-trimethoxybenzene.

Such donor compounds are preferably used in a concentration of from 0.01 to 5%, especially in a concentration of from 0.05 to 0.50%, based on the formulation.

Further examples of suitable photosensitisers (d) are

1. Thioxanthones thioxanthone, 2-isopropylthioxanthone, 2-chlorothioxanthone, 2-dodecylthioxanthone, 2,4-diethylthioxanthone, 2,4-dimethylthioxanthone, 1-methoxycarbonylthioxanthone, 2-ethoxycarbonylthioxanthone, 3-(2-methoxyethoxycarbonyl)-thioxanthone, 4-butoxycarbonylthioxanthone, 3-butoxycarbonyl-7-methylthioxanthone, 1-chloro-4-propoxy-thioxanthone, 1-cyano-3-chlorothioxanthone, 1-ethoxycarbonyl-3-chlorothioxanthone, 1-ethoxycarbonyl-3-ethoxythioxanthone, 1-ethoxycarbonyl-3-aminothioxanthone, 1-ethoxy-carbonyl-3-phenylsulfurylthioxanthone, 3,4-di[2-(2-methoxyethoxy)ethoxycarbonyl]thiox-anthone, 1-ethoxycarbonyl-3-(1-methyl-1-morpholinoethyl)-thioxanthone, 2-methyl-6-dimethoxymethylthioxanthone, 2-methyl-6-(1,1-dimethoxybenzyl)-thioxanthone, 2-morpholinomethylthioxanthone, 2-methyl-6-morpholinomethylthioxanthone, N-allylthioxanthone-3,4-dicarboximide, N-octylthioxanthone-3,4-dicarboximide, N-(1,1,3,3-tetramethylbutyl)-thioxanthone-3,4-dicarboximide, 1-phenoxythioxanthone, 6-ethoxycarbonyl-2-methoxythioxanthone, 6-ethoxycarbonyl-2-methylthioxanthone, 1,3-dimethyl-2-hydroxy-9H-thioxanthen-9-one-2-ethylhexyl ether, thioxanthone-2-polyethylene glycol ester, 2-hydroxy-3-(3,4-dimethyl-9-oxo-9H-thioxanthon-2-yloxy)-N,N,N-trimethyl1-propanaminium chloride;

2. Benzophenones benzophenone, 4-phenylbenzophenone, 4-methoxybenzophenone, 4,4'-dimethoxy-benzophenone, 4,4'-dimethylbenzophenone, 4,4'-dichlorobenzophenone, 4,4'-dimethyl-aminobenzophenone, 4,4'-diethylaminobenzophenone, 4-methylbenzophenone, 2,4,6-trimethylbenzophenone, 4-(4-methylthiophenyl)-benzophenone, 3,3'-dimethyl-4-methoxybenzophenone, methyl-2-benzoyl benzoate, 4-(2-hydroxyethylthio)-benzophenone, 4-(4-tolylthio)benzophenone, 4-benzoyl-N,N,N-trimethylbenzenemethanaminium chloride, 2-hydroxy-3-(4-benzoylphenoxy)-N,N,N-trimethyl-1-propanaminium chloride monohydrate, 4-(13-acryloyl-1,4,7,10,-13-pentaoxatridecyl)-benzophenone, 4-benzoyl-N, N-dimethyl-N-[2-(1-oxo-2-propenyl)oxy]-ethylbenzenemethanaminium chloride;

3. 3-Acylcoumarins 3-benzoylcoumarin, 3-benzoyl-7-methoxycoumarin, 3-benzoyl-5,7-di(propoxy)coumarin, 3-benzoyl-6,8-dichlorocoumarin, 3-benzoyl-6-chlorocoumarin, 3,3'-carbonyl-bis[5,7-di-(propoxy)coumarin], 3,3'-carbonyl-bis(7-methoxycoumarin), 3,3'-carbonyl-bis(7-diethylaminocoumarin), 3-isobutyroylcoumarin, 3-benzoyl-5,7-dimethoxycoumarin, 3-benzoyl-5,7-diethoxycoumarin, 3-benzoyl-5,7-dibutoxy-coumarin, 3-benzoyl-5,7-di(methoxyethoxy)-coumarin, 3-benzoyl-5,7-di(allyloxy)coumarin, 3-benzoyl-7-dimethylaminocoumarin, 3-benzoyl-7-diethylaminocoumarin, 3-isobutyroyl-7-dimethylaminocoumarin, 5,7-dimethoxy-3-(1-naphthoyl)coumarin, 5,7-dimethoxy-3-(1-naphthoyl)coumarin, 3-benzoylbenzo-[f]-coumarin, 7-diethylamino-3-thienoylcoumarin, 3-(4-cyanobenzoyl)-5,7-dimethoxycoumarin;

4. 3-(Aroylmethylene)-thiazolines 3-methyl-2-benzoylmethylene-β-naphthothiazoline, 3-methyl-2-benzoylmethylene-benzo-thiazoline, 3-ethyl-2-propionylmethylene-β-naphthothiazoline;

5. Other carbonyl compounds acetophenone, 3-methoxyacetophenone, 4-phenylacetophenone, benzil, 2-acetyl-naphthalene, 2-naphthaldehyde, 9,10-anthraquinone, 9-fluorenone, dibenzosuberone, xanthone, 2,5-bis(4-diethylaminobenzylidene)cyclopentanone, α-(para-dimethyl-aminobenzylidene)ketones, such as 2-(4-dimethylaminobenzylidene)-indan-1-one or 3-(4-dimethylamino-phenyl)-1-indan-5-yl-propenone, 2-benzoyl-3-(4-dimethylaminophenyl)-2-propene-nitrile, 3-phenylthiophthalimide, N-methyl-3,5-di(ethylthio)phthalimide, N-methyl-3,5-di(ethylthio)phthalimide.

The sensitisers (d) described above are customary in the art and are accordingly used in amounts customary in the art, preferably in a concentration of from 0.05 to 5%, especially in a concentration of from 0.1 to 2%, based on the composition.

The compositions according to the invention may additionally comprise further photo-initiators (e), such as, for example, cationic photoinitiators, photo acid-formers and free-radical photoinitiators as co-initiators in amounts of from 0.01 to 15%, preferably from 0.1 to 5%.

Examples of cationic photoinitiators and acid-formers are phosphonium salts, diazonium salts, pyridinium salts, sulfonium salts, ferrocenium salts, e.g. ($\eta^6$-isopropylbenzene)($\eta^5$-cyclopentadienyl)-iron-II hexafluorophosphate $^{RTM}$Irgacure 261, nitrobenzylsulfonates, alkyl- and aryl-N-sulfonyloxyimides and further known alkylsulfonic acid esters, haloalkylsulfonic acid esters, 1,2-disulfones, oxime sulfonates, benzoin tosylate, tolylsulfonyloxy-2-hydroxy-2-methyl-1-phenyl-1-propanone and further known beta-ketosulfones, beta-sulfonylsulfones, bis(alkylsulfonyl)diazomethane, bis(4-tert-butyl-phenyl-sulfonyl)-diazomethane, benzoyl-tosyl-diazomethane, iminosulfonates and imidosulfonates and trichloromethyl-s-triazines and other haloalkyl-group-containing compounds and further compounds mentioned under (b1).

Examples of free-radical photoinitiators as co-initiators are carbonyl compounds, as described in U.S. Pat. No. 4,560,709, 1-benzoylcyclohexanol, 2-benzoyl-2-propanol, oligo[2-hydroxy-2-methyl-1-[4-(1-methylvinyl)phenyl]propanone] and 2-hydroxy-1-[3-[4-(2-hydroxy-2-methyl-propionyl)phenyl]-1,1,3-trimethyl-indan-5-yl]-2-methyl-propan-1-one.

The compositions according to the invention may be used for a variety of purposes, for example as printing inks, such as screen-printing inks, flexo printing inks or offset printing inks, as clear lacquer, as coloured surface-coating compositions, as white surface-coating compositions, e.g. for wood or metal, as powder coating compositions, as paint, inter alia for paper, wood, metal or plastics, as daylight-curable paint for marking structures and roads, for photographic reproduction processes, for holographic recording materials, for image-recording processes or for the production of printing plates that are to be developed with organic solvents or using aqueous-alkaline media, in the production of masks for screen-printing, as dental filling compounds, as radiation-curable adhesives, as pressure-sensitive adhesives, as anti-adhesive coatings, as laminating resins, as photoresists, e.g. galvano-resists, etch resists or permanent resists, liquid films and dry films, as photostructurable dielectrics, and as solder masks for electronic circuits, as resists in the manufacture of colour filters for any type of screen or for producing structures in the manufacture of plasma displays and electroluminescent displays, in the manufacture of optical switches, optical gratings (interference gratings), in the coating or sealing of electronic components, e.g. as electroinsulating compounds, or as coatings for optical fibres, for coil coating, as indicator systems for UV radiation, X-rays and electron beams, and in the manufacture of three-dimensional articles, e.g. for stereolithography and for composites, e.g. for composites reinforced with glass or carbon or graphite fibres. The compositions are also suitable for the manufacture of optical lenses, e.g. contact lenses or Fresnel lenses, and also in the manufacture of medical apparatus, aids or implants.

The photocurable compositions according to the invention are suitable, for example, as coating materials for all kinds of substrates, for example wood, textiles, paper, ceramics, glass, marble, plastics, such as polyester, polyethylene terephthalate, polyolefins or cellulose acetate, especially in the form of films, and metals, such as Al, Cu, Ni, Fe, Zn, Mg or Co and GaAs, Si or $SiO_2$, to which a coating is to be applied or an image is to be applied by imagewise exposure, or to which a structured resist layer is to be applied.

The coating of the substrates can be effected by applying a liquid composition, a solution or suspension to the substrate. The choice of solvent and the concentration are governed chiefly by the nature of the composition and by the coating method. The solvent should be inert, that is to say it should not enter into any chemical reaction with the components and it should be capable of being removed again upon drying after the coating operation.

Examples of suitable solvents are ketones, ethers and esters, such as methyl ethyl ketone, isobutyl methyl ketone, cyclopentanone, cyclohexanone, 2-heptanone, methyl amyl ketone, N-methylpyrrolidone, gamma-butyrolactone, dioxane, tetrahydrofuran, 2-methoxyethanol, 2-ethoxyethanol, 1-methoxy-2-propanol, 1,2-dimethoxyethane, acetic acid ethyl ester, acetic acid n-butyl ester, propylene glycol monomethyl ether acetate, lactic acid ethyl ester, propylene carbonate and 3-ethoxy-propionic acid ethyl ester.

After coating of the substrates, the solvent is generally removed by drying.

The formulation is applied uniformly to a substrate by known coating methods, for example by spin-coating, immersion, knife coating, curtain pouring, brush application or spraying, especially by electrostatic spraying and reverse-roll coating, and by electrophoretic deposition. It is also possible to apply the photosensitive layer to a temporary flexible support and then coat the final substrate, e.g. a copper-laminated printed circuit board, by transferring the layer by lamination.

The amount applied (layer thickness) and the type of substrate (layer support) are dependent upon the desired field of use. The layer thickness range generally includes values from about 0.1 $\mu$m to more than 100 $\mu$m, preferably from 0.5 micrometre to 50 micrometres. In the manufacture of three-dimensional articles, e.g. by stereolithography, the dimensions of the articles that can be obtained are limited only by the size of the exposure apparatus.

The radiation-sensitive compositions according to the invention are used, for example, as negative resists that have very high photosensitivity and that can be developed in an aqueous-alkaline medium without swelling. They are suitable as photoresists for electronics, such as galvanoresists, etch resists, and in liquid and dry films, solder resists, as resists in the production of colour filters for any type of screen, or to form structures in the manufacture of plasma displays and electroluminescent displays, in the manufacture of printing plates, e.g. offset printing plates, in the manufacture of printing moulds for letterpress printing, flatbed printing, intaglio printing, flexo printing or screen-printing moulds, the production of relief copies, e.g. for the production of texts in braille, for the production of stamps, for use in the etching of mouldings or for use as a microresist in the manufacture of integrated switching circuits. The compositions can also be used as photostructurable dielectrics, for encapsulating materials or as an insulating coating in the manufacture of computer chips, printed circuits and other electrical or electronic components. The possible layer supports and processing conditions for the coated substrates vary accordingly.

The compounds according to the invention are also used in the manufacture of single- or multi-layer materials for image recording or image reproduction (copies, reprography), which may be monochromatic or polychromatic. Included therein are materials for holographic storage of information, e.g. for holographic images or 3-dimensional holographic data storage. Such materials can also be used in colour test systems. In that technology it is also possible to use formulations that comprise microcapsules and, to produce the image, a thermal step can be carried out after the exposure step. Such systems and technologies and their use are described, e.g., in U.S. Pat. No. 5,376,459.

For photographic recordings of information there are used, for example, films of polyester, cellulose acetate or plastics-coated papers; for offset printing moulds there is used specially treated aluminium; for the production of printed circuits there are used copper-coated laminates; and for the production of integrated switching circuits there are used silicon wafers. The layer thicknesses for photographic materials and offset printing moulds are generally from about 0.5 $\mu$m to 10 $\mu$m, and for printed circuits from 1.0 $\mu$m to about 100 $\mu$m.

The invention relates also to the use of compounds of formula I as radiation-sensitive acid donors in the manufacture of surface-coating compositions, printing inks, printing plates, dental compounds, stereolithography resins, adhesives, anti-adhesive coatings, colour filters, resist materials or image-recording materials.

The invention relates also to a coated substrate that is coated on at least one surface with a composition according to the invention, and to a method for the production of relief images wherein a composition according to the invention is applied to a substrate and is then exposed image-wise.

The expression "image-wise exposure" includes irradiation through a mask that contains a predetermined pattern, for example a diapositive, a metal mask, a chrome mask on a transparent support, exposure by means of a laser beam that is moved, for example controlled by a computer, over the surface of the coated substrate and in that manner produces an image, and irradiation with computer-controlled electron beams. Images can also be produced by interference between two beams or images, for example for holographic uses. It is also possible to use liquid crystal masks that can be actuated pixel by pixel to produce digital images, as described, for example, by A. Bertsch, J. Y. Jezequel, J. C. Andre in Journal of Photochemistry and Photobiology A: Chemistry 1997, 107, pp. 275–281 and by K. P. Nicolay in Offset Printing 1997, 6, pp. 34–37.

As already mentioned, the compounds of formula I can be used especially also as acid donors in photoresists. Resist systems can be obtained by image-wise exposure of formulations comprising compounds of formula I and a subsequent development step. The term "photoresist" is not limited to the chemically enhanced resists described in greater detail below, but includes all resist materials in which reactions are initiated by the radiation-chemical production of acid and that, in a development step, result in a difference in solubility between exposed and non-exposed regions. For example, also included are resists that can be processed in an aqueous medium, as described, for example, in U.S. Pat. No. 5,998,092 and in SPIE, Vol. 3999, pp. 569–578 (2000) as well as resists based on a Pinacol rearrangement, as described, for example, in SPIE, Vol. 3999, pp. 62–73 (2000).

Accordingly, the invention relates also to a photoresist that comprises a compound of formula I as radiation-sensitive acid donor.

A chemically enhanced photoresist is to be understood as being a resist formulation in which the radiation-sensitive component provides a catalytic amount of acid, which in turn catalyses a chemical reaction of at least one acid-sensitive component of the resist. This results in a difference in the solubility of the irradiated and non-irradiated portions of the resist. As a result of the catalytic nature of that process, an acid molecule can initiate reactions at many sites because it diffuses through the reactive polymer matrix from one reaction site to the next, provided it is not captured or destroyed by secondary reactions. Even a low acid concentration is therefore sufficient to obtain large differences in solubility between irradiated and non-irradiated portions of the resist. It is therefore generally sufficient to add only a small amount of latent acid compound. It is necessary, however, for the latent acid donors to be chemically and thermally stable until they are being irradiated. It is also necessary for the latent catalysts to be readily soluble in the liquid resist formulation and in the solid resist film in order to avoid the formation of particles which would adversely affect the use of the resists in microelectronic processing processes.

It will be clear from the above remarks that chemical and thermal stability of the latent acid donor is essential for its use in chemically enhanced photoresists.

The difference in solubility between exposed and non-exposed areas in the resist, which results from the action of the acid-catalysed reaction, depends upon the other components in the resist. If the compositions according to the invention comprise components that increase the solubility of the composition in the developer after irradiation and optionally after thermal aftertreatment, then it is a positive photoresist.

The invention accordingly relates also to a positive photoresist.

If, however, the components of the composition lower the solubility in the developer after irradiation and optionally after thermal aftertreatment, then it is a negative photoresist. The invention accordingly relates also to a negative photoresist.

An overview of chemically enhanced photoresists can be found, for example, in: H. Ito, IBM Journal of Research and Development, Vol. 41, No. 1/2, page 69 (1997); H. Ito, SPIE Vol. 3678, page 2 (1999); for negative resists in: J. M. Shaw et al. IBM Journal of Research and Development, Vol. 41, No. 1/2, page 81 (1997).

A monomeric, oligomeric or polymeric compound that, in non-exposed portions, lowers the rate of solubility of an alkali-soluble binder polymer also present in the resist formulation, and that is itself alkali-insoluble in the non-exposed portions, with the result that the resist film is retained in the non-exposed portions after development in an alkaline solution, but that is cleaved in the presence of an acid or is capable of being rearranged in such a manner that the reaction product becomes soluble in an alkaline developer, is referred to hereinafter as a solubility inhibitor.

The invention also includes a chemically enhanced positive photoresist composition that can be developed in an alkaline medium, which photoresist composition comprises (a3) at least one polymer having acid-labile groups that decompose in the presence of an acid and increase the solubility of the resist film in an alkaline developer solution in the irradiated areas, and (b) at least one compound of formula I.

The invention relates also to a chemically enhanced positive photoresist composition that can be developed in an alkaline medium, which photoresist composition comprises (a4) at least one monomeric or oligomeric solubility inhibitor having at least one acid-labile group that decomposes in the presence of an acid and that increases the solubility in aqueous-alkaline developer solutions, and at least one alkali-soluble polymer, and (b) at least one compound of formula I.

The invention relates also to a chemically enhanced positive photoresist composition that can be developed in an alkaline medium, which photoresist composition comprises (a3) at least one polymer having acid-labile groups that decompose in the presence of an acid and increase the solubility in an aqueous-alkaline developer solution in the exposed area;

(a4) a monomeric or oligomeric solubility inhibitor having at least one acid-labile group that decomposes in the presence of an acid and that increases the solubility in an aqueous-alkaline developer solution in the exposed area;

(a5) an alkali-soluble monomeric, oligomeric or polymeric compound in a concentration that keeps the resist film in non-exposed areas completely insoluble in an alkaline developer, and (b) at least one compound of formula I.

The invention relates also to a chemically enhanced photoresist composition comprising (a3) at least one polymer having an acid-labile group that decomposes in the presence of an acid and increases the solubility in an aqueous-alkaline developer solution, and/or (a4) at least one monomeric or oligomeric solubility inhibitor having an acid-labile group that decomposes in the presence of an acid and increases the solubility in an aqueous-alkaline developer solution, and/or (a5) at least one alkali-soluble monomeric, oligomeric or polymeric compound; and (b) as photosensitive acid donor at least one compound of formula I.

The compositions may comprise, in addition to component (b), other photosensitive acid donors and/or other additives (c) and/or photosensitisers (d).

Appropriate suitable additives (c) and photosensitisers (d) have been described hereinabove.

Such chemically enhanced positive photoresist systems are described, for example, in E. Reichmanis, F. M. Houlihan, O. Nalamasu, T. X. Neenan, Chem. Mater. 1991, 3, 394; or in C. G. Willson, "Introduction to Microlithography, 2nd. Ed.; L. S. Thompson, C. G. Willson, M. J. Bowden, Eds., Amer. Chem. Soc., Washington D.C., 1994, p. 139.

Suitable examples of acid-labile groups that decompose in the presence of an acid and form aromatic hydroxyl groups, carboxyl groups, keto groups and aldehyde groups and increase the solubility in aqueous-alkaline developer solutions include alkoxyalkyl ether groups, benzyl ether groups, tetrahydrofuranyl ether groups, tetrahydropyranyl ether groups, tert-alkyl ester groups, 2-methyl-2-adamantyl ester groups, 8-ethyl-8-tricyclo-decanyl ester groups, trityl ether groups, silyl ether groups, alkylcarbonate groups, such as, for example, tert-butyloxycarbonyloxy groups, trityl ester groups, silyl ester groups, alkoxy-methyl ester groups, cumyl ester groups, acetal groups, ketal groups, tetrahydropyranyl ester groups, tetrafuranyl ester groups, tertiary alkyl ether groups, tertiary alkyl ester groups, etc.

The polymers having functional groups that decompose under the action of an acid in order to increase the solubility of the resist film comprising that polymer in an alkaline developer solution and that can be added to the compositions of the present invention can carry the acid-labile groups in the polymer backbone and/or in the side chains. The acid-labile groups are preferably situated in the side chain of the polymer.

Suitable polymers having acid-labile groups can be obtained by polymer-analogous reactions in which some or all of the alkali-soluble groups are converted into the acid-labile group in question. Also possible is the direct preparation by (co)polymerisation of monomers that already contain the acid-labile groups. Examples of the preparation have been published in EP 254853, EP 878738, EP 877293, JP-A-2-25850, JP-A-3-223860, and JP-A-4-251259.

In polymers containing, for example, silyl ether, acetal, ketal and alkoxyalkyl ester groups (socalled low-activation energy blocking groups—protecting groups having low activation energy), such protecting groups are cleaved in the presence of an acid even at relatively low temperatures upon heating after exposure (generally between room temperature and 110° C.). Polymers that carry tert-butyl ester groups, adamantyl ester groups or tert-butyloxycarbonyl groups (TBOC groups) or other ester groups that carry a secondary or tertiary carbon atom in addition to the oxygen atom of the ester bond (so-called high-activation energy blocking groups—protecting groups having high activation energy) generally require heating to achieve complete cleavage of the protecting groups in the presence of an acid after exposure. Hybrid systems in which both high-activation energy protecting groups and low activation energy protecting groups are present in the same polymer can also be used. So-called "dual-mode" protecting groups are also known, which combine within them a readily cleavable bond, e.g. in an acetal group, and a bond that is more difficult to cleave, e.g. in a tert-butyl ester group, as described, for example, in "Proceedings of SPIE", Advances in Resist Technology and Processing XVII, Vol. 3999, Part One, pages 579–590. Feb. 28–Mar. 1, 2000. Mixtures of polymers having different protecting group chemistry can also be used in the photosensitive compositions according to the invention.

Preferred polymers having acid-labile protecting groups are polymers and copolymers comprising the following different monomer types:

1) monomers that contain acid-labile groups that decompose in the presence of an acid and increase the solubility in an aqueous-alkaline developer solution, and
2) monomers that are free of acid-labile groups and free of groups that contribute to the solubility in an alkaline solution, and/or
3) monomers that contribute to the aqueous-alkali solubility of the polymer.

Examples of monomers of type 1) are those already described above as a suitable component (a2).

Examples of comonomers of type 2) are:
aromatic vinyl monomers, such as styrene, α-methylstyrene, acetoxystyrene, α-methylnaphthalene, acenaphthalene, vinyl ethers, such as ethyl vinyl ether and 3,4-dihydro-2 H-pyran, cyclohexylvinyl ether, cycloolefins, such as norbornene, 2-hydroxy-5-norbornene, 2-norbornen-5-yl-(2-hydroxyethyl)carboxylate, vinyl alicyclic compounds, such as vinyl norbornane, vinyl adamantane, vinyl cyclohexane, alkyl (meth)acrylates, such as methyl methacrylate, acrylonitrile, vinyl cyclohexane, vinyl cyclohexanol, and maleic acid anhydride.

Examples of comonomers of type 3) are:
vinyl aromatic compounds, such as hydroxystyrene, acrylic acid compounds, such as methacrylic acid, ethylcarbonyloxystyrene and derivatives thereof and cycloolefinic acids, such as 5-norbornene-2-carboxylic acid. Such polymers are described, for example, in U.S. Pat. No. 5,827,634, U.S. Pat. No. 5,625,020, U.S. Pat. No. 5,492,793, U.S. Pat. No. 5,372,912, EP 660187, U.S. 5,679,495, EP 813113 and EP 831369. Further examples are crotonic acid, isocrotonic acid, 3-butenoic acid, acrylic acid, 4-pentenoic acid, propionic acid, 2-butynoic acid, maleic acid, fumaric acid and acetylenecarboxylic acid. The polymers that are suitable in the composition according to the invention are not, however, limited to the examples given above.

The content of acid-labile monomer in the polymer can vary within a wide range and is dependent upon the content of other comonomers and the alkali-solubility of the protected polymer. Generally the content of monomer having acid-labile groups in the polymer is from 5 to 60 mol %.

The copolymers having acid-labile groups preferably have a $M_w$ of from about 3000 to about 200,000, especially from about 5000 to about 50,000 and a molecular weight distribution of about 3 or less, especially about 2 or less. Non-phenolic monomers, e.g. a copolymer of alkyl acrylate, such as, for example, tert-butyl acrylate or tert-butyl methacrylate, and an alicyclic vinyl compound, such as a vinyl norbonanyl or vinylcyclohexanol compound, can be obtained by free-radical polymerisation or other known processes and advantageously have a $M_w$ value of from about 8000 to about 50 000, and a molecular weight distribution of about 3 or less.

Other comonomers can be added advantageously in a suitable amount in order, for example, to control the glass transition temperature or the like.

In the present invention it is also possible to use mixtures of two or more polymers having acid-labile groups. For example, a mixture of polymers having acid-labile groups that cleave very readily, such as acetal groups or tetrahydropyranyloxy groups, and a polymer having acid-labile groups that cleave less readily, such as, for example, tertiary alkyl ester groups, can be used. It is also possible to use acid-labile groups of different sizes by mixing two or more polymers having different acid-labile groups, such as, for example, a tert-butyl ester group and a 2-methyl-adamantyl group or a 1-ethoxy-ethoxy group and a tetrahydropyranyloxy group. A mixture of non-crosslinked resin and crosslinked resin can also be used.

According to the invention, the proportion of such polymers is preferably from about 30 to 99% by weight, especially from 50 to 98% by weight, based on the solids content. An alkali-soluble resin or an alkali-soluble monomeric or oligomeric compound without acid-labile groups can also be introduced into the composition, for example in order to control the alkali-solubility. Examples of polymer mixtures having different acid-labile groups can be found, for example, in EP 780732, EP 679951 and U.S. Pat. No. 5,817,444.

Monomeric and oligomeric solubility inhibitors (a4) are preferably used in the composition according to the invention.

Suitable monomeric or oligomeric solubility inhibitors (a4) in the composition according to the invention are compounds having at least one acid-labile group that cleaves in the presence of acid and increases solubility in an aqueous-alkaline developer solution. Examples thereof include alkoxymethyl ether groups, tetrahydrofuranyl ether groups, tetrahydro-pyranyl ether groups, alkoxyethyl ether groups, trityl ether groups, silyl ether groups, alkylcarbonate groups, trityl ester groups, silyl ester groups, alkoxymethyl ester groups, vinyl carbamate groups, tertiary alkyl carbamate groups, tritylamino groups, cumyl ester groups, acetal groups, ketal groups, tetrahydropyranyl ester groups, tetrafuranyl ester groups, tertiary alkyl ether groups, tertiary alkyl ester groups, etc. The molecular weight of the acid-cleavable solubility inhibitors suitable in the present invention is about 3000 or less, especially from about 100 to 3000, preferably from about 200 to 2500.

Examples of monomeric and oligomeric solubility inhibitors having acid-labile groups are described, for example, as compounds of formulae (I) to (XVI) in EP 831369. Other suitable examples of such compounds are given in U.S. Pat. No. 5,356,752, U.S. Pat. No. 5,037,721, U.S. Pat. No. 5,015,554, JP-A-1-289946, JP-A-1-289947, JP-A-2-2560, JP-A-3-128959, JP-A-3-158855, JP-A-3-179353, A-3-191351, JP-A-3-200251, JP-A-3-200252, JP-A-3-200253, JP-A-3-200254, JP-A-3-200255, JP-A-3-259149, JA-3-279958, JP-A-3-279959, JP-A-4-1650, JP-A-4-1651, JP-A-11260, JP-A-4-12356, JP-A-4-123567, JP-A-1-289946, JP-A-3-128959, JP-A-3-158855, JP-A-3-179353, JP-A-3-191351, JP-A-3-200251, JP-A-3-200252, JP-A-3-200253, JP-A-3-200254, JP-A-3-200255, JP-A-3-259149, JA-3-279958, JP-A-3-279959, JP-A-4-1650, JP-A-4-1651, JP-A-11260, JP-A-4-12356, JP-A-4-12357 and Japanese Patent Application Nos. 3-33229, 3-230790, 3-320438, 4-254157, 4-52732, 4-103215, 4-104542, 4-107885, 4-107889, 4-152195, 4-254157, 4-103215, 4-104542, 4-107885, 4-107889 and 4-152195. Suitable for resists in the short-wave UV range are, for example, especially compounds such as tert-butyl cholate, tert-butyl deoxycholate and tert-butylcholate glutarate dimers (see, e.g., SPIE Vol. 3999, p. 127 (2000).

The composition according to the invention may also comprise polymeric solubility inhibitors, for example polyacetals, as described in U.S. Pat. No. 5,354,643, or poly-N,O-acetals, as described in U.S. Pat. No. 5,498,506, in combination with an alkali-soluble polymer, and also in combination with a polymer having acid-labile groups that increase the solubility of the resist film in the developer after exposure, or in a combination of the two types of polymer described.

In the compositions according to the invention the content of solubility inhibitor is from about 3 to 55% by weight, especially from about 5 to 45% by weight, preferably from 10 to 35% by weight, based on the solids content, when solubility inhibitors having acid-labile groups are used in combination with alkali-soluble polymers and/or polymers having acid-labile groups.

Preferably soluble polymers (a5) are used in the compositions according to the invention in an aqueous-alkaline solution. Examples thereof include novolak resins, hydrogenated novolak resins, acetonepyrogallol resins, poly(o-hydroxystyrene), poly(m-hydroxystyrene), poly(p-hydroxystyrene), hydrogenated poly(hydroxystyrenes), halo- or alkyl-substituted poly(hydroxystyrenes), hydroxystyrene/N-substituted maleimide copolymers, o-/p- and m/p-hydroxystyrene copolymers, partially o-alkylated poly(hydroxystyrenes), [e.g. o-methylated, o-(1-methoxy) ethylated, o-(1-ethoxy)ethylated, o-2-tetrahydropyranylated and o-(tert-butoxycarbonyl)methylated poly (hydroxystyrenes) having a substitution proportion of about from 5 to 30 mol % of hydroxyl groups], o-acylated poly (hydroxystyrenes) [e.g. o-acetylated and o-(tert-butoxy) carbonylated poly(hydroxystyrenes) having a substitution proportion of about from 5 to 30 mol % of hydroxyl groups], styrene/maleic acid anhydride copolymers, styrene/hydroxystyrene copolymers, α-methylstyrene/hydroxystyrene copolymers, carboxylated methacrylic resins, and derivatives thereof. Also suitable are poly(meth) acrylic acid [e.g. poly(acrylic acid)], (meth)acrylic acid/(meth)acrylate copolymers [e.g. acrylic acid/-methyl acrylate copolymers, methacrylic acid/methyl methacrylate copolymers or methacrylic acid/methyl methacrylate/tert-butyl methacrylate copolymers], (meth)acrylic acid/alkene copolymers [e.g. acrylic acid/ethylene copolymers], (meth) acrylic acid/(meth)-acrylamide copolymers [e.g. acrylic acid/acrylamide copolymers], (meth)acrylic acid/vinyl chloride copolymers [e.g. acrylic acid/vinyl chloride copolymers], (meth)acrylic acid/vinyl acetate copolymers [e.g. acrylic acid/vinyl acetate copolymers], maleic acid/vinyl ether copolymers [e.g. maleic acid/methyl vinyl ether copolymers], maleic acid monoester/methyl vinyl ester copolymers [e.g. maleic acid monomethyl ester/methyl vinyl ether copolymers], maleic acid/(meth)acrylic acid copolymers [e.g. maleic acid/acrylic acid copolymers or maleic acid/methacrylic acid copolymers], maleic acid/(meth)acrylate copolymers [e.g. maleic acid/methyl acrylate copolymers], maleic acid/vinyl chloride copolymers, maleic acid/vinyl acetate copolymers and maleic acid/alkene copolymers [e.g. maleic acid/ethylene copolymers and maleic acid/1-chloropropene copolymers]. The polymers suitable for the compositions according to the invention are in no way limited, however, to the examples given above.

Especially preferred as alkali-soluble polymers (a5) are novolak resins, poly(m-hydroxystyrene), poly(p-hydroxystyrene), copolymers of the corresponding hydroxystyrene monomers, for example with p-vinylcyclohexanol, alkyl-substituted poly(hydroxystyrenes), partially o- or m-alkylated and o- or m-acylated poly(hydroxystyrenes), styrene/hydroxystyrene copolymer and α-methylstyrene/hydroxystyrene copolymers. The novolak compounds are obtainable, for example, by addition condensation reactions of one or more monomers as main constituent(s) with one or more aldehydes in the presence of an acid catalyst.

Examples of monomers that are suitable for the preparation of alkali-soluble resins are hydroxylated aromatic compounds, such as phenol, cresols, that is to say m-cresol, p-cresol and o-cresol, dimethylphenols (xylenols), e.g. 2,5-dimethylphenol, 3,5-dimethylphenol, 3,4-di-methylphenol and 2,3-dimethylphenol, alkoxyphenols, e.g. p-methoxyphenol, m-methoxyphenol, 3,5-dimethoxyphenol, 2-methoxy-4-methylphenol, m-ethoxyphenol, p-ethoxyphenol, m-propoxyphenol, p-propoxyphenol, m-butoxyphenol and p-butoxyphenol, dialkylphenols, e.g. 2-methyl-4-isopropylphenol, and other hydroxylated aromatic compounds including m-chlorophenol, p-chlorophenol, o-chlorophenol, dihydroxybiphenyl, bisphenol-A, phenylphenol, resorcinol and naphthene. Such compounds can be used alone or in mixtures of two or more. The monomers for novolak resins are not limited to the examples mentioned above.

Suitable examples of aldehydes for polycondensation with phenolic compounds in the preparation of novolaks are formaldehyde, p-formaldehyde, acetaldehyde, propionaldehyde, benzaidehyde, phenylacetaldehyde, α-phenylpropionaldehyde, β-phenylpropion-aldehyde, o-hydroxybenzaldehyde, m-hydroxybenzaldehyde, p-hydroxybenzaldehyde, o-chlorobenzaldehyde, m-chlorobenzaldehyde, p-chlorobenzaldehyde, o-nitrobenzaldehyde, m-nitrobenzaldehyde, o-methylbenzaldehyde, m-methylbenzaldehyde, p-methylbenzaldehyde, p-ethylbenzaldehyde, p-, n-butylbenzaldehyde, furfural, chloroacetaldehyde and acetals derived therefrom, such as chloroacetaldehyde diethyl acetal. Preference is given to formaldehyde.

Those aldehydes can be used alone or in a combination of two or more. Examples of suitable acid catalysts include hydrochloric acid, sulfuric acid, formic acid, acetic acid and oxalic acid.

The average molecular weight of the resulting novolaks is advantageously in the range of about from 1000 to 30,000, preferably about from 2000 to 20,000.

The poly(hydroxystyrenes), and derivatives and copolymers thereof, as described above as alkali-soluble polymers (other than novolak resins), advantageously have average molecular weights of from about 2000 or higher, especially from 4000 to 200,000, preferably from 5000 to 50,000. When a polymer film having improved heat-resistance is to be produced, the average molecular weight is advantageously at least 5000 or more.

In the context of the present invention, the term "average molecular weight" is to be understood as the molar mass determined by gel permeation chromatography (calibrated with polystyrene standard).

In the compositions according to the invention, the alkali-soluble polymers can be used in mixtures of two or more.

Advantageously, the proportion of alkali-soluble polymer is up to 80% by weight, especially up to 60% by weight, preferably up to 40% by weight, based on the solids content of the formulation (i.e. excluding solvent) when there is used a mixture of alkali-soluble polymer and a polymer that contains groups that decompose under the action of an acid in order to increase the solubility in an alkaline developer solution.

When an alkali-soluble polymer is used together with a solubility inhibitor, without a polymer that has groups that decompose under the action of an acid, the proportion of alkali-soluble polymer is advantageously from 40 to 90% by weight, especially from 50 to 85% by weight, preferably from 60 to 80% by weight.

The proportion of compounds of formula I (component (b)) in the positive resist formulation is advantageously from about 0.01 to 20% by weight, based on the solids content in the photoresist.

The use of the iodonium salts of formula I in chemically enhanced systems based on the principle of the removal of protecting groups from a polymer normally results in a positive resist Positive resists are preferred to negative resists in many applications, especially because of their better resolution. There is, however, also interest in producing negative images using the positive resist mechanism, in order to combine the advantages of the good resolution of the positive resist with the properties of a negative resist. This is effected, for example, by the introduction of a so-called image-reversal step, as described, for example, in EP 361906. For that purpose, the resist material, after image-wise exposure, is treated, for example, with a gaseous base, before development, the acid that is formed being neutralised image-wise. The entire resist is then exposed and subjected to thermal treatment, and the negative image is developed in the customary manner.

Acid-sensitive components that form negative resists are generally compounds that are capable of undergoing a crosslinking reaction with themselves and/or with one or more further components in the composition when they are catalysed by an acid (e.g. the acid formed by exposure of the compounds of formula I according to the invention). Compounds of that kind are, for example, the known acid-curable resins, such as acrylate, polyester, alkyd, melamine, urea, epoxy and phenolic resins or mixtures thereof. Amino resins, phenolic resins and epoxy resins are especially suitable. Acid-curable resins of that kind are generally known and are described, for example, in "Ullmann's Encyclopädie der technischen Chemie", Edition 4, Vol. 15 (1978), pp. 613–628. The crosslinking components should advantageously be present in a concentration of about from 2 to 40% by weight, preferably from 5 to 30% by weight, based on the solids content of the negative resist formulation.

The invention accordingly also includes a chemically enhanced negative photoresist that can be developed in an alkaline medium, which negative photoresist comprises (a6) an alkali-soluble resin as crosslinking component, (a7) a component that undergoes a crosslinking reaction with itself and/or with the crosslinking component under the action of acid, and (b) as photosensitive acid donor a compound of formula I.

The composition may comprise, in addition to component (b), further photosensitive acid donors and/or further additives (c), and photosensitisers (d). Suitable components (c) and (d) have been described above.

There come into consideration as component (a7) the compounds given above in the description of component (a1).

Especially preferred acid-curable resins (a7) are amino resins, such as non-etherified or etherified melamine, urea, guanidine or biuret resins, especially methylated melamine resins or butylated melamine resins, suitable glycolurils (tetrahydroimidazo[4,5-d]imidazole-2,5-(1H,3H-diones) and urones. In this context, the term "resin" means both customary technical mixtures that generally also include oligomers, and pure and high-purity compounds. N-Hexa(methoxymethyl)melamine and tetramethoxymethylglucoril, and N,N'-dimethoxymethylurone are the preferred acid-curable resins.

The concentration of the compound of formula I in the negative resist is advantageously from about 0.1 to 30% by weight, especially up to 20% by weight, preferably from 1 to 15% by weight, based on the total solids content of the compositions.

The negative resist compositions may optionally comprise a film-forming polymeric crosslinking agent (binder) (a6). This will preferably be an alkali-soluble phenolic resin. Also highly suitable for that purpose are, for example, novolaks derived from an aldehyde, e.g. acetaldehyde or furfuraldehyde, especially from formaldehyde, and from a phenol, e.g. unsubstituted phenol, mono- or di-chlorosubstituted phenol, such as p-chloro-phenol, phenol mono- or di-substituted by $C_1$–$C_9$alkyl, such as o-, m- or p-cresol, the various xylenols, p-tert-butylphenol, p-nonylphenol, p-phenylphenol, resorcinol, bis(4-hydroxyphenyl)methane or 2,2-bis(4-hydroxyphenyl)propane. Also suitable are homo- and co-polymers based on ethylenically unsaturated phenols, e.g. homopolymers of vinyl- and 1-propenyl-substituted phenols, such as p-vinylphenol or p-(1-propenyl)phenol or copolymers of those phenols with one or more ethylenically unsaturated compounds, e.g. styrenes. The proportion of crosslinking agent is generally within a range of about from 30 to 95% by weight, especially from 40 to 80 % by weight.

An especially preferred negative resist formulation comprises from 0.5 to 15% by weight of a compound of formula I (component (b)), from 40 to 99% by weight of a phenolic resin as crosslinking agent (component (a6)), and from 0.5 to 30% by weight of a melamine resin (component (a7)), the percentages relating to the total solids content of the formulation.

Compounds of formula I can also be used as acid donors that can be activated photochemically for the crosslinking of, for example, poly(glycidyl) methacrylates in negative resist systems. Such crosslinking reactions are disclosed, for example, by Chae et al. in Pollimo 1993, 17(3), 292.

The positive and negative photoresist formulations may comprise, in addition to component (b), further photosensitive acid donors (b1), further additives (c), sensitisers (d) and/or other photoinitiators (e).

The invention accordingly also relates to chemically enhanced resist compositions, as described above, that comprise, in addition to components (a1) or (a2) and (b), or components (a3), (a4), (a5) and (b), or components (a6), (a7) and (b), further additives (c), further photosensitive acid donors (b1), other photoinitiators (e), and/or sensitisers (d).

The compounds of formula I can be used in the compositions according to the invention in combination with further known photolatent acid donors (b1), such as, for example, further onium salts, 6-nitrobenzylsulfonates, bis-sulfonyldiazomethane compounds, oxime sulfonates, etc. Examples of known photolatent acids for chemically enhanced photoresists are to be found, for example, in U.S. 5,731,364, U.S. 5,800,964, EP 704762, U.S. 5,468,589, U.S. 5,558,971, U.S. 5,558,976 and especially EP 794457 and EP 795786.

When mixtures of compounds of formula I (b) with other photolatent acids (b1) are used, the ratio of (b) to (b1) is, for example, from 1:99 to 99:1.

Examples of suitable photolatent acids (b1) include
(1) onium salt compounds, e.g.
further iodonium salts, sulfonium salts, phosphonium salts, diazonium salts, pyridinium salts. Preference is given to diphenyliodonium triflate, diphenyliodonium pyrenesulfonate, diphenyliodonium dodecylphenylsulfonate, triphenylsulfonium triflate, triphenylsulfonium hexafluoroantimonate, diphenyliodonium hexafluoroantimonate, triphenylsulfonium naphthalenesulfonate, (hydroxyphenyl) benzylmethylsulfonium toluylsulfonate, etc.
(2) halogen-containing compounds
haloalkyl-group-containing heterocyclic compounds, haloalkyl-group-containing hydrocarbon compounds, etc. Preference is given to (trichloromethyl)-s-triazine derivatives, such as phenyl-bis(trichloromethyl)-s-triazine, methoxyphenyl-bis(trichloromethyl)-s-triazine, naphthyl-bis-(trichloromethyl)-s-triazine, etc.; 1,1-bis(4-chlorophenyl)-2,2,2-trichloroethane, etc.;
(3) sulfone compounds, e.g.
β-ketosulfones, β-sulfonylsulfones and α-diazo derivatives thereof, etc. Preference is given to phenacylphenylsulfone, mesitylphenacylsulfone, bis(phenylsulfonyl)methane, bis(phenylsulfonyl)diazomethane.
(4) sulfonate compounds, e.g.
alkylsulfonic acid esters, haloalkylsulfonic acid esters, arylsulfonic acid esters, iminosulfonates, imidosulfonates, etc. Preference is given to imidosulfonates, e.g. N-(trifluoromethylsulfonyloxy)succinimide, N-(trifluoromethylsulfonyloxy)phthalimide, N-(trifluoromethylsulfonyloxy)naphthylimide, N-(trifluoromethylsulfonyloxy)diphenylmaleimide, N-(trifluoromethyl-sulfonyloxy)-bicyclo-[2.2. 1 ]-hept-5-ene-2,3-dicarboximide, N-(trifluoromethylsulfonyloxy)-7-oxabicyclo-[2.2.1 ]-hept-5-ene-2,3-dicarboximide, N-(trifluoromethylsulfonyloxy)7-oxabicyclo-[2.2.1 ]-hept-5-ene-2,3-dicarboximide, N-(trifluoromethylsulfonyl-oxy)-bicyclo-[2.2.1 ]-heptan-5,6-oxy-2,3-dicarboximide, N-(camphanylsulfonyloxy)suc-cinimide, N-(camphanylsulfonyloxy)phthalimide, N-(camphanylsulfonyloxy)naphthylimide, N-(camphanylsulfonyloxy)diphenylmaleimide, N-(camphanylsulfonyloxy)bicyclo-[2.2.1]-hept-5-ene-2,3-dicarboximide, N-(camphanylsulfonyloxy)-7-oxabicyclo-[2.2.1]-hept-5-ene-2,3-dicarboximide, N-(camphanylsulfonyloxy)-7-oxabicyclo-[2.2.1]hept-5-ene-2,3-dicarbox-imide, N-(camphanylsulfonyloxy)-bicyclo-[2.2.1]-heptan-5,6-oxy-2,3-dicarboximide, N-(4-methylphenylsulfonyloxy)succinimide, N-(4-methylphenylsulfonyloxy)phthalimide, N-(4-methylphenylsulfonyloxy)naphthylimide, N-(4-methylphenylsulfonyloxy)naphthylimide, N-(4-methylphenylsulfonyloxy)diphenylmaleimide, N-(4-methylphenylsulfonyloxy)-bicyclo-[2.2. 1]-hept-5-ene-2,3-dicarboximide, N-(4-methylphenylsulfonyloxy)-7-oxabicyclo-[2.2.1]-hept-5-ene-2,3-dicarboximide, N-(4-methylphenylsulfonyl-oxy)-bicyclo-[2.2. 1]-heptan-5,6-oxy-2,3-dicarboximide, N-(2-trifluoromethylphenylsulfonyloxy)succinimide, N-(2-trifluoromethyl-phenylsulfonyloxy)naphthylimide, N-(2-trifluoromethylphenylsulfonyloxy)diphenylmaleimide, N-(2-trifluoromethylphenylsulfonyloxy)-bicyclo-[2.2.1]-hept-5-ene-2,3-dicarboximide, N-(2-trifluoromethylphenylsulfonyloxy)-7-oxabicyclo-[2.2.1]-hept-5-ene-2,3-dicarboximide, N-(2-trifluoromethylphenylsulfonyloxy)-bicyclo-[2.2.1]-heptan-5,6-oxy-2,3-dicarboximide, etc.

Further suitable sulfonate compounds are, for example, benzoin tosylate, pyrogallol tristriflate, pyrogallolmethanesulfonic acid triester, nitrobenzyl-9,10-diethyloxyanthracyl-2-sulfonate, α-(4-toluenesulfonyloxyimino)-benzyl cyanide, α-(4-toluenesu lfonyloxyimino)-4-methoxybenzyl cyanide, α-(4-toluene-sulfonyloxyimino)-2-thienylmethyl cyanide, α-(methylsulfonyloxyimino)-1-cyclohexenylacetonitrile, α-(butylsulfonyloxyi mino)-1-cyclopentenyl-acetonitrile, (4-methylsulfonyloxyimino-cyclohexa-2,5-dienylidene)-phenyl-acetonitrile, (5-methylsulfonyloxyimino-5H-thiophen-2-ylidene)-phenyl-acetonitrile, (5-methylsulfonyl-oxyimino-5H-thiophen-2-ylidene)-(2-methylphenyl)-acetonitrile, (5-methylsulfonyloxyimino-5H-thiophen-2-ylidene)-(2-chlorophenyl)-acetonitrile, etc.

In the compositions according to the invention, special preference is given to sulfonate compounds, such as pyrogallolmethanesulfonic acid triester, N-(trifluoromethylsulfonyloxy)bicyclo-[2.2.1]-hept-5-ene-2,3-dicarboximide, N-(camphanylsulfonyloxy)-naphthylimide, N-(2-trifluoromethylphenylsulfonyloxy)phthalimide, N-(trifluoromethyl-sulfonyloxy)-bicyclo-[2.2.1]-hept-5-ene-2,3-dicarboximide, N-(camphanylsulfonyloxy)-naphthylimide, N-(2-trifluoromethylphenylsulfonyloxy) phthalimide, etc.
(5) quinonediazide compounds,
e.g. 1,2-quinonediazidesulfonic acid ester compounds of polyhydroxy compounds. Preference is given to compounds having a 1,2-quinonediazidesulfonyl group, e.g. a 1,2-benzoquinonediazide-4-sulfonyl group, a 1,2- naphthoquinonediazide-4-sulfonyl group, a 1,2-naphthoquinonediazide-5-sulfonyl group, a 1,2-naphthoquinonediazide-6-sulfonyl group, etc.

Special preference is given to compounds having a 1,2-naphthoquinonediazide-4-sulfonyl group or a 1,2-naphthoquinonediazide-5-sulfonyl group. Especially suitable are 1,2-quinonediazidesulfonic acid esters of (poly) hydroxyphenylarylketones, such as 2,3,4-trihydroxybenzophenone, 2,4,6-trihydroxybenzophenone, 2,3,4,4'-tetrahydroxybenzo-phenone, 2,2', 3,4-tetrahydroxybenzophenone, 2,3,4,4'-tetrahydroxybenzophenone, 2,2', 4,4'-tetrahydroxybenzophenone, 2,2', 3,4,4'-pentahydroxybenzophenone, 2,2', 3,2',6'-pentahydroxybenzophenone, 2,3,3', 4,4', 5'-hexahydroxybenzophenone, 2,3', 4,4', 5', 6-hexahydroxybenzophenone, etc.; 1,2-quinonediazidesulfonic acid esters of bis[(poly)-hydroxyphenyl]alkanes, such as bis(4-hydroxyphenyl) ethane, bis(2,4-dihydroxyphenyl)-ethane, 2,2-bis(4-hydroxyphenyl)propane, 2,2-bis(2,4-dihydroxyphenyl) propane, 2,2-bis(2,3,4-trihydroxyphenyl)propane, etc.; 1,2-quinonediazidesulfonic acid esters of (poly) hydroxyphenylalkanes, such as 4,4'-dihydroxytriphenylmethane, 4,4'4"-trihydroxy-triphenylmethane, 4,4'5,5'-tetramethyl-2,2'2"-trihydroxytriphenylmethane, 2,2,5,5'-tetramethyl-4,4'4"-trihydroxytriphenylmethane, 1,1,1-tris(4-hydroxyphenyl) ethane, 1,1-bis(4-hydroxyphenyl)-1-phenylethane, 1,1-bis (4-hydroxyphenyl)-1-(4-[1-(hydroxyphenyl)-1-methylethyl]phenyl)ethane, etc; 1,2-quinonediazidesulfonic acid esters of (poly)hydroxy-phenylflavanes, such as 2,4,4-trimethyl-2', 4'7-trihydroxy-2-phenylflavane, 2,4,4-trimethyl-2',4',5',6,7-pentahydroxy-2-phenylflavane, etc.

Further suitable additives (c) are as described above.

Further examples of basic organic compounds that can be used in the resist compositions according to the present invention are compounds that are stronger bases than phenol, especially nitrogen-containing bases. Such compounds may be ionic, such as tetraalkyl-ammonium salts, or non-ionic. Preference is given to nitrogen-containing bases that, per molecule, have two or more nitrogen atoms in different chemical environments. Special preference is given to compounds comprising at least one substituted or unsubstituted amino group and at least one nitrogen-containing ring structure, as well as to compounds having at least one alkylamino group. Examples thereof include guanidine, aminopyridine, aminoalkylpyridines, aminopyrrolidine, indazole, imidazole, pyrazole, pyrazine, pyrimidine, purine, imidazoline, pyrazoline, piperazine, aminomorpholine and aminoalkylmorpholines. Both the unsubstituted and the substituted derivatives thereof are suitable. Preferred substituents are amino groups, aminoalkyl groups, alkylamino groups, aminoaryl groups, aryl-amino groups, alkyl groups, alkoxy groups, acyl groups, acyloxy groups, aryl groups, aryloxy groups, nitro, hydroxy and cyano. Specific examples of especially preferred basic compounds are guanidine, 1,1-dimethylguanidine, 1,1,3,3-tetramethylguanidine, 2-amino-pyridine, 3-aminopyridine, 4-aminopyridine, 2-dimethylaminopyridine, 4-dimethylamino-pyridine, 2-diethylaminopyridine, 2-(aminomethyl)pyridine, 2-amino-3-methylpyridine, 2-amino-4-methylpyridine, 2-amino-5-methylpyridine, 2-amino-6-methylpyridine, 3-amino-ethylpyridine, 4-aminoethylpyridine, 3-aminopyrrolidine, piperazine, N-(2-aminoethyl)-piperazine, N-(2-aminoethyl)piperidine, 4-amino-2,2,6,6-tetramethylpiperidine, 4-piperidinopiperidine, 2-iminopiperidine, 1-(2-aminoethyl)pyrrolidine, pyrazole, 3-amino-5-methylpyrazole, 5-amino-3-methyl-1-p-tolylpyrazole, pyrazine, 2-(aminomethyl)-5-methyl-pyrazine, pyrimidine, 2,4-diaminopyrimidine, 4,6-dihydroxypyrimidine, 2-pyrazoline, 3-pyrazoline, N-aminomorpholine and N-(2-aminoethyl)morpholine.

Other examples can be found in DE 4408318, U.S. Pat. No. 5,609,989, U.S. Pat No. 5,556,734, EP 762207, DE 4306069, EP 611998, EP 813113, EP 611998 and U.S. Pat No. 5,498,506. The basic compounds suitable for the compositions according to the invention are not limited, however, to those described above.

The nitrogen-containing basic compounds may be used alone or in a combination of two or more. The proportion of those compounds is generally about from 0.001 to 10 parts by weight, especially from 0.01 to 5 parts by weight, per 100 parts by weight of the photosensitive composition according to the invention (without the solvent).

The composition may also comprise an organic basic compound that decomposes under the action of actinic radiation ("suicide base"), as described, for example, in EP 710885, U.S. Pat No. 5,663,035, U.S. U.S. Pat. No. 5,595,855, U.S. Pat. No. 5,525,453 and EP 611998.

Suitable examples of dyes (c) are those mentioned above as well as oil-soluble dyes and basic dyes, e.g. Oil Yellow #101, Oil Yellow #103, Oil Pink #312, Oil Green BG, Oil Blue BOS, Oil Blue #603, Oil Black BY, Oil Black BS, Oil Black T-505 (all from Orient Chemical Industries Ltd., Japan), crystal violet (CI42555), methyl violet (CI42535), rhodamine B (CI45170B), malachite green (CI42000) and methylene blue (CI52015).

Examples of sensitisers (d) are as described above and are, for example, p,p'-tetramethyldiaminobenzophenone, p,p'-tetraethylethylaminobenzophenone, anthrone, pyrene, perylene, phenothiazine, benzil, acridine orange, benzoflavin, cetoflavin T, 9,10-diphenylanthracene, 9-fluorenone, phenanthrene, acetophenone, 2-nitrofluorene, 5-nitroacenaphthene, benzoquinone, 2-chloro-4-nitroaniline, N-acetyl-p-nitroaniline, p-nitroaniline, N-acetyl-4-nitro-1-naphthylamine, picramide, anthraquinone, 2-ethylanthraquinone, 2-tert-butyl-anthraquinone, 1,2-benzanthraquinone, 3-methyl-1,3-diaza-1,9-benzanthrone, dibenzalacetone, 1,2-naphthoquinone, 3-acylcoumarin derivatives, 3,3'-carbonyl-bis(5,7-dimethoxycarbonyl-coumarin), 3-(aroylmethylene) thiazolines, eosin, rhodamine, erythrosin and coronene.

Suitable sensitisers are not, however, limited to those examples. Such sensitisers can also be used as photoabsorbers for the absorption of specific UV rays emitted by light sources. In that case, the photoabsorber reduces the reflection of light from the substrate and lessens the effect of multiple reflection inside the resist film. This reduces the effect of standing waves.

Further suitable additives (c) are acid-amplifiers, compounds that accelerate the formation of acid or increase the acid concentration. Such compounds can be used in the resist compositions according to the invention, but can also be advantageous in other applications for the compositions according to the invention, such as in coatings. Examples of such compounds are described by Arimitsu, K. et al. in J. Photopolym. Sci. Technol. 1995, 8, p. 43ff.; by Kudo, K. et al. in J. Photopolym. Sci. Technol. 1995, 8, p. 45ff.; by W. Huang et al in SPIE Vol. 3999, pp. 591–597 (2000) and by Ichimura, K. et al. in Chem: Letters 1995, p. 551ff.

Normally the compositions according to the invention are dissolved in a suitable solvent before application to the substrate. Examples of such solvents include ethylene dichloride, cyclohexanone, cyclopentanone, 2-heptanone, γ-butyrolactone, methyl ethyl ketone, ethylene glycol monomethyl ether, ethylene glycol monoethyl ether, 2-methoxyethyl acetate, 2-ethoxyethyl acetate, 2-ethoxyethanol, diethyl glycol dimethyl ether, ethylene glycol monoethyl ether acetate, propylene glycol monomethyl ether, propylene glycol monomethyl ether acetate, toluene, ethyl acetate, methyl lactate, ethyl lactate, methylmethoxy propionate, ethylethoxy propionate, methyl pyruvate, ethyl pyruvate, propyl pyruvate, N,N-dimethylformamide, dimethyl sulfoxide, N-methylpyrrolidone and tetrahydrofuran. Such solvents can be used individually or in combinations. Preferred examples thereof are esters, such as 2-methoxyethyl acetate, ethylene glycol monoethyl ether acetate, propylene glycol monomethyl ether acetate, methylmethoxy propionate, ethylethoxy propionate and ethyl lactate.

A surfactant may be added to the solvent. Examples of suitable surfactants are non-ionic surfactants, such as polyoxyethylene alkyl ethers, e.g. polyoxyethylene lauryl ether, polyoxyethylene stearyl ether, polyoxyethylene acetyl ether and polyoxyethylene oleyl ether; polyoxyethylene alkyl aryl ethers, e.g. polyoxyethylene octyl phenol ether and polyoxyethylene nonyl phenol ether; polyoxyethylene/polyoxypropylene block copolymers, sorbitol/fatty acid esters, e.g. sorbitol monolaurate, sorbitol monopalmitate, sorbitol monostearate, sorbitol monooleate, sorbitol trioleate; fluorochemical surfactants, such as F-top EF301, EF303 and EF352 (New Akita Chemical Company, Japan), Megafac F171 and F17.3 (Dainippon Ink & Chemicals, Inc,. Japan), Fluorad FC 430 and FC431 (Sumitomo #M Ltd., Japan), Asahi Guard AG710 and Surflon S-382, SC101, SC102, SC103, SC104, SC105 and SC106 (Asahi Grass Col, Ltd., Japan); organosiloxane polymer KP341 (Shin-Etsu Chemical Co., Ltd., Japan); and acrylic or methacrylic (co)polymers Poly-flow Now.75 and NO.95 (Kyoeisha Chemical Co., Ltd., Japan). Generally the proportion of surfactant in the composition is about 2 parts by weight or less, e.g. 0.1 part by weight or less, per 100 parts by weight of solids content in the composition. The surfactants may be used individually or in combinations.

The solution of the composition according to the invention is applied uniformly to a substrate by means of generally known methods already described above. Suitable layer thicknesses have also already been indicated above.

After coating, the solvent is usually removed by heating and a layer of the photoresist remains on the substrate. The drying temperatures must, of course, be lower than the temperatures at which constituents of the resist formulation can decompose or react. Normally the drying temperatures vary within a range of about from 60 to 160° C.

The exposure of the coated substrates has already been described above. After exposure and, if necessary after the thermal treatment, the exposed sites of the composition (in the case of the positive resist) or the non-exposed sites of the composition (in the case of the negative resist) are removed using a developer in a manner generally known to a person skilled in the art.

In order to accelerate the catalytic reaction and thus to ensure the development of a sufficient difference in solubility between exposed and non-exposed areas of the resist coating, the coating is preferably heated before development. It is also possible to carry out heating during the exposure. Generally temperatures of from 60 to 160° C. are used. The optimum duration of heating depends upon the heating method used and can be determined by the person skilled in the art by simple experiments. It normally ranges from a few seconds to several minutes, e.g. from 10 to 300 seconds when a heating plate is used, and, e.g., from 1 to 30 minutes when a circulated-air oven is used.

Development is then carried out, wherein the portions of the coating that are soluble in the developer are removed. If necessary, the development step can be accelerated by gentle movement of the sample, careful brushing of the coating in the developer bath or by development in a spray developing apparatus. Aqueous-alkali developer fluids customary in the art can be used for that purpose. Examples thereof include sodium and potassium hydroxide, the corresponding carbonates, hydrogen carbonates, silicates and metasilicates, metal-free bases, such as ammonium compounds, or amines, such as ethylamine, n-propylamine, diethylamine, di-n-propylamine, triethylamine, methyldiethylamine, alkanolamines, e.g. di-methylethanolamine, triethanolamine, quaternary ammonium hydroxides, e.g. tetramethylammonium hydroxide or tetraethylammonium hydroxide. The developer solutions are normally up to 0.5N, but are generally diluted before use in a suitable manner. For example, solvents having a normality of about from 0.1 to 0.3 are very suitable. The choice of developer will depend upon the nature of the photocurable coating, especially upon the nature of the crosslinking agent or the resulting photolysis products. The aqueous developer solutions may, if necessary, also comprise small amounts of wetting agents and/or organic solvents. Examples of typical organic solvents that may be added to the developer solutions include cyclohexanone, 2-ethoxyethanol, toluene, acetone, isopropanol and mixtures of two or more such solvents. A typical aqueous/organic developer system is a system based on Butylcellosolve$^{RTM}$/water.

The invention relates also to a method of manufacturing a photoresist by (1) applying a composition as described above to a substrate;
(2) heating the composition to a temperature of from 60° C. to 160° C.;
(3) carrying out image-wise exposure with light of a wavelength of from 150 nm to 1500 nm;
(4) optionally heating the composition to temperatures of from 60° C. to 160° C.; and
(5) subsequently developing with a solvent or an aqueous alkaline developer.

The photoresist compositions can be used on all types of substrate and with all irradiation techniques known to the person skilled in the art. For example, semiconductor substrates can be used, such as silicon, gallium arsenide, germanium, indium antimonide; also substrates covered by oxide or nitride layers, such as silicon dioxide, silicon nitride, titanium nitride, siloxanes, and metal substrates and metal-coated substrates coated with metals such as aluminium, copper, tungsten, etc. The substrate can also be coated with polymeric materials, for example with organic antireflective coatings, insulation layers and dielectric coatings made of polymeric materials.

The photoresist layer can be irradiated by all customary techniques, such as direct writing, i.e. with a laser beam or projection lithography in step-and repeat mode or scanning mode, or by contact printing through a mask.

In the case of projection lithography, a large number of optical conditions can be selected, such as coherent, partially coherent or incoherent radiation. This includes non-axial irradiation techniques, for example annular illumination and quadrupolar irradiation where the radiation is allowed to pass through only certain regions of the lens, excluding the center of the lens.

The mask used to produce the pattern can be a hard mask or a flexible mask. The mask can include transparent, semi-transparent and opaque patterns. The pattern size can include also patterns that are at or below the resolution limit of the projection optics and are arranged on the mask in a certain manner in order to modify the aerial image, intensity and phase modulation of the radiation after having it has passed through the mask. This includes phase-shift masks and half-tone phase-shift masks.

The process for forming an image on the photoresist composition can be used to generate patterns of any desired geometry and shape, for example dense and isolated lines, contact holes, channels, incisions, dots, etc.

Preference is given to a method wherein the image-wise exposure is effected by monochromatic or polychromatic radiation in the wavelength range of from 190 to 450 nm, especially from 190 to 260 nm.

The invention relates also to the use of compounds of formula I as described above as photolatent acid donors in the polymerisation or crosslinking of cationically or acid-catalytically polymerisable or crosslinkable compounds or to increase the solubility of compounds that increase their solubility in a developer under the action of acid, and also to a method for the photopolymerisation or crosslinking of cationically or acid-catalytically polymerisable or crosslinkable compounds under the action of electromagnetic radiation, in which method a compound of formula I is used as photolatent acid donor.

The UV irradiation to release the acid is generally effected with light of a wavelength of from 157 to 600 nm. Suitable radiation is present, for example, in sunlight or light from artificial light sources. A large number of widely varying types of light source may be used. Point sources and also planiform radiators (lamp carpets) are suitable. Examples thereof include: carbon arc lamps, xenon arc lamps, medium-, high- and low-pressure mercury lamps, doped where appropriate with metal halides (metal halide lamps), microwave-excited metal vapour lamps, excimer lamps, superactinic fluorescent tubes, fluorescent lamps, argon incandescent lamps, flashlamps, photographic flood lights, electron beams and X-rays.

The distance between the lamp and the substrate to be exposed can vary according to the intended use and the type and strength of the lamp and may be, for example, from 2 cm to 150 cm. Laser light sources, for example excimer lasers, are also suitable. Lasers in the visible range can also be used.

The following Examples illustrate the invention further. As in the remainder of the description and in the patent claims, amounts given in parts or percentages relate to weight, unless otherwise mentioned. When alkyl or alkoxy radicals having more than three carbon atoms are indicated in the Examples without reference to their isomeric form, the data relate to the respective n-isomers.

EXAMPLE 1

Preparation of (4-isobutylphenyl)-p-tolyl-iodonium Hexafluorophosphate 45.22 g (0.21 mol) of 4-iodotoluene in 326 g of 75% sulfuric acid are introduced into a 750 ml flask having a reflux condenser, a thermometer, a stirrer and a nitrogen supply. 29.2 g (0.22 mol) of isobutylbenzene are then added, and the heterogeneous mixture is cooled to 1 0° C. 94.7 g (0.41 mol) of ammonium peroxodisulfate are added in portions so that the temperature does not exceed 15° C. The reaction mixture is stirred at room temperature for 5 hours. The reaction mixture is then added over the course of 40 minutes at 5–10° C. to a well stirred suspension of 38.18 g (0.21 mol) of potassium hexafluorophosphate in 600 ml of water and 500 ml of acetic acid ethyl ester. The mixture is maintained at room temperature for 1.5 hours, and the phases are separated. The organic phase is washed with water and 5% sodium hydrogen carbonate, and the solvent is removed in vacuo. 89 g (0.18 mol; 86%) of p-isobutylphenyl-p-tolyl-iodonium hexafluorophosphate are obtained in the form of a brownish resin. The product is purified further by chromatography (dichloromethane:ethanol 95:5 on $SiO_2$) or by recrystallisation from chloroform/hexane.

An analytically pure sample has the following physical properties: white powder, melting point (m.p.) 90–92° C. The $^1$H-NMR spectrum ($CDCl_3$) exhibits shift signals at the following values δ [ppm]: 7.9 (4H, m, ArH), 7.23 (4H, m, ArH), 2.45 (2H, d, J=6.2Hz, $CH_2$), 1.81 (1H, m, $CH(CH_3)_2$), 0.85 (6H, d, J=6.2 Hz, 2 $CH_3$). Elemental analysis: calculated for $C_{17}H_{20}F_6I$ P (496.21)

|         | C [%] | H [%] | F [%] | P [%] |
|---------|-------|-------|-------|-------|
| calc.:  | 41.15 | 4.06  | 22.97 | 6.24  |
| found:  | 41.15 | 4.19  | 22.82 | 5.95  |

EXAMPLES 2–13

The compounds of Examples 2–13 are prepared in a manner analogous to that described in Example 1, from the appropriate substituted aromatic compounds. The structures and the physical data are given in Table 1

TABLE 1

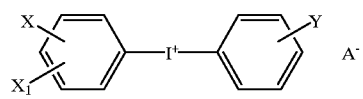

|  |  |  |  | elemental analysis calc. [%] found [%] | | |
|---|---|---|---|---|---|---|
| Ex. | X/X$_1$ | Y | A | physical properties | C | H | F |
| 2 | 4-C(CH$_3$)$_3$ /H | 4-CH$_3$ | PF$_6$ | white powder, m.p. 105–108° C. | 41.15 41.27 | 4.06 4.23 | 22.97 22.81 |
| 3 | 4-C(CH$_3$)$_2$C$_2$H$_5$ /H | 4-CH$_3$ | PF$_6$ | whitish powder, m.p. 94-98° C. | 42.37 42.73 | 4.35 4.59 | 22.34 20.44 |

TABLE 1-continued $$\text{structure: } X, X_1\text{-substituted phenyl—I}^+\text{—phenyl-Y} \quad A^-$$

| Ex. | X/X$_1$ | Y | A | physical properties | C (calc./found) | H (calc./found) | F (calc./found) |
|---|---|---|---|---|---|---|---|
| 4 | 4-cyclohexyl/H | 4-CH$_3$ | PF$_6$ | glassy, brown resin | 43.70 / 46.41 | 4.25 / 4.66 | 21.83 / 19.84 |
| 5 | 4-CH$_2$—CH(CH$_3$)$_2$/H | 2-CH$_3$ | PF$_6$ | whitish powder, m.p. 120° C. | 41.15 / 40.99 | 4.06 / 4.00 | 22.97 / 22.80 |
| 6 | 4-CH$_2$—CH(CH$_3$)$_2$/H | 3-CH$_3$ | PF$_6$ | glassy, brown resin | 41.15 / 41.66 | 4.06 / 3.87 | 22.97 / 22.64 |
| 7 | 4-C(CH$_3$)$_3$/H | 3-CH$_3$ | PF$_6$ | yellow crystals m.p. 104–106° C. | 41.15 / 41.53 | 4.06 / 4.27 | 22.97 / 22.07 |
| 8 | 4-CH$_2$—CH(CH$_3$)$_2$/H | 4-C$_2$H$_5$ | PF$_6$ | glassy, brown resin | 42.37 / 43.02 | 4.35 / 4.32 | 22.34 / 21.70 |
| 9 | 4-CH$_2$—CH(CH$_3$)$_2$/H | 4-CH$_3$ | SbF$_6$ | viscous oil | 34.79 / 34.75 | 3.43 / 3.47 | 19.42 / 19.29 |
| 10 | 4-CH$_2$—CH(CH$_3$)$_2$/H | 4-CH—(CH$_3$)$_2$ | PF$_6$ | yellow resin | 43.53 / 43.55 | 4.61 / 4.77 | 21.74 / 20.63 |
| 11 | 4-CH$_2$—CH(CH$_3$)$_2$/H | 4-CH$_3$ | 4-CH$_3$—Ph—SO$_3$ | glassy, brown resin | 55.18 / 54.75 | 5.21 / 5.43 | — / — |
| 12 | 4-CH$_2$—CH(CH$_3$)$_2$/H | 4-CH$_3$ | (±) camphor sufonate | glassy, brown resin | 55.67 / 55.71 | 6.06 / 6.21 | — / — |
| 13 | 4-CH(CH$_3$)$_2$/2-CH(CH$_3$)$_2$ | 4-CH$_3$ | PF$_6$ | beige powder, m.p. 137–141° C. | 43.53 / 43.68 | 4.61 / 4.71 | 21.74 / 21.24 |

EXAMPLE 14

(4-Methylphenyl)(4'-isobutylphenyl)iodonium Nonaflate 4.5 g of potassium nonaflate is suspended in 15 ml of water. To the solution is added 4.93 g of the crude (4-methylphenyl)(4'-isobutylphenyl)iodonium hydrogensulfate dissolved in 10 ml of methanol. The mixture is stirred for 1 hour at room temperature. 15 ml of methylene chloride is added to the solution and stirred overnight at room temperature. The product is extracted with methylene chloride and the organic layer is washed with water, dried over MgSO$_4$, and concentrated. The residue is purified by flash chromatography on silica gel with methylene chloride and ethanol (95:5) as eluent, yielding 2.46 g (3.8 mmol; 34%) of (4-methylphenyl)(4'-isobutylphenyl)iodonium nonaflate as a brown resin. The structure is confirmed by the $^1$H-NMR spectrum (CDCl$_3$). δ [ppm]: 0.88 (d, 6H), 1.84 (m,1H), 2.41 (s, 3H), 2.50 (d, 2H), 7.21–7.26 (m, 4H), 7.84 (d, 4H). Elemental analysis: calculation for C$_{21}$H$_{20}$O$_3$F$_9$SI

| | C [%] | H [%] | F [%] |
|---|---|---|---|
| calc.: | 38.78 | 3.10 | 26.29 |
| found: | 38.80 | 3.09 | 26.17 |

EXAMPLE 15

Photocuring of a White-pigmented Epoxy Resin Composition

A photocurable formulation is prepared by mixing the following components 36.0 parts of bisphenol-A epoxy resin ($^{RTM}$Araldit GY 250, from Vantico), 14.4 parts of trimethylolpropane triglycidyl ether ($^{RTM}$Grinolit V51-31, from Emschemie), 9.6 parts of C$_{12/14}$alkyl glycidyl ether ($^{RTM}$Grinolit Epoxid 8, from Emschemie), and 40.0 parts of rutile titanium dioxide ($^{RTM}$R-TC2, from Tioxide).

The formulation is heated to 50° C. and is mixed uniformly by stirring for 20 minutes in the presence of glass beads as an aid. 1.5% of the compound of Example 1 and 0.5% of a mixture of 2-isopropylthioxanthone and 4-isopropylthioxanthone ($^{RTM}$Quantacure ITX) are added and dissolved in the formulation by stirring. The formulation is applied, in a layer thickness of 12 micrometers, to a brushed aluminium sheet and is irradiated in an exposure apparatus (from Fördertechnik) with a fusion M-lamp (120 W/cm). For that purpose, the sample is passed under the lamp on a conveyor belt moving at a speed of 10 m/min. A fully cured, non-sticky surface is obtained. The gloss of the surface is measured at an angle of incidence of 60° and is 97.

EXAMPLE 16

The procedure is analogous to that of Example 15, but the compound of Example 7 is used instead of the compound of Example 1. A fully cured, non-sticky surface is obtained. The gloss of the surface is measured at an angle of incidence of 60° and is 96.

EXAMPLE 17

Determination of the Photocrosslinking Reactivity in a Cationically Curable Epoxy Composition A composition is prepared by dissolving 30.0 parts of epoxycresol novolak ($^{RTM}$Araldit ECN 9699, Vantico), 10.0 parts of 3,4-epoxycyclohexylmethyl-3,4-epoxycyclohexane carboxylate ($^{RTM}$Araldit CY 179, Vantico)

in 60 parts of propylene glycol methyl ether acetate (PGMEA).

To that solution there are added 1.6 parts of an iodonium salt and 0.4 part of a mixture of 2-isopropylthioxanthone and 4-isopropylthioxanthone ($^{RTM}$Quantacure ITX), which are dissolved in the formulation by stirring.

The composition is applied by spin-coating, using a Convac Spincoater at 500 revolutions per minute for 30 seconds, to a 0.5 mm thick, anodically oxidised aluminium sheet and is then dried at 110° C. on a heating plate for 60 seconds to form a solid, 5 micrometer thick film. The film is then exposed on the aluminium substrate for 100 seconds in a Süss contact exposure apparatus MJB 55 with a high-pressure mercury lamp through a 15-step quartz grey-scale transmission mask ("Photoresist Multi Density Step Tablet") using the contact process, and is then heated on a heating plate for 120 seconds at 140° C. and subsequently developed for 30 seconds in propylene glycol methyl ether acetate (PGMEA), then rinsed for 10 seconds with 2-propanol and finally blown dry with compressed air. The lowest transmission value at which the film under the corresponding transmission field of the mask is not dissolved away is then determined. That value characterises the crosslinking reactivity and thus the photosensitivity of the photoinitiator used, with the composition otherwise being the same and the process conditions being the same. Since the exposure energy is calculated by the following formula $$\text{exposure energy} = \text{transmission} \times \text{exposure time} \times \text{intensity of radiation}$$
$$[\text{mJ/cm}^2] \qquad\qquad [\text{s}] \qquad [\text{mW/cm}^2]$$

then, with the same exposure time and the intensity of radiation being constant, the minimum exposure dose required for full crosslinking (photosensitivity) is directly proportional to the minimum transmission value at which the film is still sufficiently crosslinked not to be dissolved away in the developer. The radiation intensity in all the tests is constant at 7.1 mW/cm$^2$, determined using an OAI 400 probe and an OAI Powermeter.

Since the exposure in the Suss contact exposure apparatus used is distinguished by the fact that, during the irradiation, virtually no heat acts upon the substrate, the thermal activation of the epoxy crosslinking by the photochemically generated cations can take place, separately from the irradiation, in a highly reproducible manner in a subsequent heating step on a temperature-controlled heating plate. With the heating temperature and time being the same, differences in the measured transmission step at which the film is not yet dissolved away from the substrate during development can therefore be directly attributed to the different photosensitivity or photoreactivity of the iodonium salts or sensitisers used.

The transmission value can thus be used directly as a relative measure of the exposure energy required. A low value corresponds to high photoreactivity (high photosensitivity) and a high value corresponds to low photoreactivity (low photosensitivity) of the photoinitiator (iodonium salt) or sensitiser system used.

The so-determined minimum transmission values necessary for crosslinking are given for examples of the iodonium salts according to the invention in Table 2 and for comparative examples in Table 2a, in the column "Example 17".

EXAMPLE 18

Determination of the Photocrosslinking Reactivity in an Acid-catalytically Curable Melamine Resin-phenolic Resin Composition A composition is prepared by dissolving 18.0 parts of poly(4-hydroxystyrene) (VP 8000, Nisso)

8.3 parts of hexamethoxymethylmelamine resin ($^{RTM}$Cymel 301, Dyno Cyanamid)

1.2 parts of an iodonium salt photoinitiator according to the invention, and 0.3 part of a mixture of 2-isopropylthioxanthone and 4-isopropylthioxanthone ($^{RTM}$Quantacure ITX)

in 72.2 parts of propylene glycol methyl ether acetate (PGMEA) and is applied analogously to Example 17. The layer thickness of that composition after spin-coating and drying of the layer is 5 micrometers. Before development, a post-exposure bake is carried out at 140° C. on a heating plate for a duration of 120 seconds. The layer is developed for 60 seconds in aqueous 2.38% tetramethylammonium hydroxide solution, rinsed in water for 10 seconds and blown dry with compressed air. Determination of the minimum transmission values necessary for crosslinking is effected as described in Example 17. The results are again given in Table 2 for the compounds according to the invention and in Table 2a for comparative examples, in each case in the column "Example 18".

The compositions according to the invention combine high photosensitivity (low minimum transmission values) for effective full crosslinking, both in epoxy curing and in acid-catalytic melamine resin curing, and do not produce any health-endangering benzene upon exposure.

TABLE 2

In each case 4% of the photoinitiator according to the invention and 1% of
RTMQuantacure ITX were used.

| Photoinitiator from Example | Structure | minimum relative exposure dose [% transmission] | |
|---|---|---|---|
| | | Example 17 | Example 18 |
| 1 | H₃C—⟨C₆H₄⟩—I⁺—⟨C₆H₄⟩—iC₄H₉  PF₆⁻ | 12 | 10 |
| 6 | H₃C—⟨C₆H₄⟩—I⁺—⟨C₆H₄⟩—iC₄H₉  PF₆⁻ | 14 | 5 |
| 5 | (2-CH₃)⟨C₆H₄⟩—I⁺—⟨C₆H₄⟩—iC₄H₉  PF₆⁻ | 12 | 5 |
| 8 | H₅C₂—⟨C₆H₄⟩—I⁺—⟨C₆H₄⟩—iC₄H₉  PF₆⁻ | 22 | 5 |
| 2 | H₃C—⟨C₆H₄⟩—I⁺—⟨C₆H₄⟩—tC₄H₉  PF₆⁻ | 14 | 20 |
| 7 | H₃C—⟨C₆H₄⟩—I⁺—⟨C₆H₄⟩—tC₄H₉  PF₆⁻ | 12 | 5 |
| 3 | H₃C—⟨C₆H₄⟩—I⁺—⟨C₆H₄⟩—C(CH₃)₂C₂H₅  PF₆⁻ | 20 | 5 |
| 4 | H₃C—⟨C₆H₄⟩—I⁺—⟨C₆H₄⟩—C₆H₁₁  PF₆⁻ | 22 | 14 |
| 10 | iH₇C₃—⟨C₆H₄⟩—I⁺—⟨C₆H₄⟩—iC₄H₉  PF₆⁻ | 25 | 14 |

TABLE 2a

Comparative Examples using iodonium salts not according to the invention
In each case 4% of the iodonium photoinitiator and 1% Quantacure ITX were used.

| Comparative compound | Formula | minimum relative exposure dose [% transmission] | |
|---|---|---|---|
| | | Example 17 | Example 18 |
| A | 4-methylphenyl-4-dodecylphenyliodonium PF$_6^-$ (H$_3$C–C$_6$H$_4$–I$^+$–C$_6$H$_4$–C$_{12}$H$_{25}$, PF$_6^-$) | 40 | 40 |
| B | 4-isobutylphenyl-4-isobutylphenyliodonium PF$_6^-$ (H$_9$C$_4^i$–C$_6$H$_4$–I$^+$–C$_6$H$_4$–$^i$C$_4$H$_9$, PF$_6^-$) | 25 | 40 |
| C | 4-isobutylphenyl-4-isobutylphenyliodonium PF$_6^-$ (H$_9$C$_4^i$–C$_6$H$_4$–I$^+$–C$_6$H$_4$–$^i$C$_4$H$_9$, PF$_6^-$) | 30 | 50 |

EXAMPLE 19

In accordance with Example 17, a formulation is prepared with (4-isobutylphenyl)-p-tolyliodonium hexafluoroantimonate from Example 9, instead of the iodonium salt of Example 1. Application and evaluation are carried out as described in Example 17. The minimum transmission required for crosslinking is only 1%.

EXAMPLE 20

In accordance with Example 17, a formulation is prepared with the iodonium salt of Example 1, but the sensitiser mixture of 2-isopropylthioxanthone and 4-isopropylthioxanthone ($^{RTM}$Quantacure ITX) is completely replaced by the same amount (1 part) of 1-chloro-4-propoxythioxanthen-9-one ($^{RTM}$Quantacure CPTX). Application and evaluation are carried out as described in Example 17. The measured minimum transmission required for crosslinking is 12%.

EXAMPLE 21

In accordance with Example 17, a formulation is prepared with the iodonium salt of Example 1, but the sensitiser mixture of 2-isopropylthioxanthone and 4-isopropylthioxanthone ($^{RTM}$Quantacure ITX) is completely replaced by the same amount (1 part) of 3,3'-carbonylbis(7-dimethylaminocoumarin). Application and evaluation are carried out as described in Example 17. The measured minimum transmission required for crosslinking is 10%.

EXAMPLE 22

In accordance with Example 17, a formulation is prepared with the iodonium salt of Example 1, the sensitiser mixture of 2-isopropylthioxanthone and 4-isopropylthioxanthone ($^{RTM}$Quantacure ITX) being completely replaced by the same amount (1 part) of 9,10-dimethoxy-2-ethylanthracene (Aldrich). Application and evaluation are carried out as described in Example 17. The measured transmission required for crosslinking is 5%.

EXAMPLE 23

Cationic Clear Lacquer Based on an Epoxidised Soybean Oil

2% of iodonium salt photoinitiator are added to every 100 parts of epoxidised soybean oil (Edenol D 81, Cognis).

The mixtures are applied to white melamine-coated chipboard panels using a 100 μm knife and are irradiated under 2×120 W/cm medium-pressure mercury lamps at a belt speed of 3×5 m/min. The initiators used and the curing results are given in the following Tables 3 (initiator according to the invention) and 3a (iodonium salts not according to the invention).

TABLE 3

| Photoinitiator from Example | | Observations after irradiation |
|---|---|---|
| 1 | H$_3$C–C$_6$H$_4$–I$^+$–C$_6$H$_4$–$^i$C$_4$H$_9$, PF$_6^-$ | well cured film |

TABLE 3a

Comparative Examples using iodonium salts not according to the invention

| Photoinitiator | | Observations after irradiation |
|---|---|---|
| D | phenyl-I+-C6H4-C12H25, PF6− | no curing |
| E | phenyl-I+-C6H4-C10H21, PF6− | no curing |
| F | phenyl-I+-C6H4-iC3H7, SbF6− | no curing |

EXAMPLE 24

A blue flexo printing ink formulation is prepared by intimately triturating:

73.2 parts of $^{RTM}$Cyracure UVR-6105 (3,4-epoxycyclohexylmethyl carboxylate, Union Carbide)

10.5 parts of $^{RTM}$Cyracure UVR-6000 (3-ethyl-3-hydroxymethyl-oxetane, Union Carbide)

5.3 parts of $^{RTM}$TONE 0301 (ε-caprolactone-triol, Union Carbide)

0.5 part of $^{RTM}$BYK 307 (polyether-modified dimethyl-polysiloxane copolymer, Byk)

10.5 parts of $^{RTM}$Irgalit Blue GLO (copper phthalocyanine, Ciba Specialty Chemicals)

and additionally 6% of (4-isobutylphenyl)-p-tolyl-iodonium hexafluorophosphate (compound of Example 1) and 0.5% of a mixture of 2-isopropylthioxanthone and 4-isopropylthioxanthone ($^{RTM}$Quantacure ITX).

The cationic printing ink is applied, in a layer thickness of 4 micrometers, to aluminium foil using a K-bar coater and is cured in an IST exposure apparatus equipped with a 120 W/cm medium-pressure mercury lamp. The printed substrate is then heated in an oven at 100° C. for 5 minutes and the fastness of the surface to wiping and resistance of the cured printing ink layer is determined by the number of double-rub tests using methyl ethyl ketone (MEK)-impregnated cellulose in which the printing ink is not removed.

In the present case, at a curing rate of 100 m/min the printing ink is fast to wiping and resistant to 12 double-rub tests with MEK.

EXAMPLE 25

A flexo printing ink is prepared and tested analogously to Example 24, but the photoinitiator of Example 1 is replaced by (4-isobutylphenyl)-p-ethylphenyliodonium hexafluorophosphate (compound of Example 8).

At a curing rate of 20 m/min, the printing ink is fast to wiping and resistant to >50 MEK double-rub tests.

EXAMPLE 26

A flexo printing ink is prepared and tested analogously to Example 24, but the photoinitiator of Example 1 is replaced by 4-tert-butylphenyl-p-tolyliodonium hexafluorophosphate (compound of Example 2).

At a curing rate of 70 m/min, the printing ink is fast to wiping and resistant to 43 MEK double-rub tests.

EXAMPLE 27

A flexo printing ink is prepared and tested analogously to Example 24, but the photoinitiator of Example 1 is replaced by 4-[2-(2-methyl)-butyl)-phenyl]-p-tolyliodonium hexafluoro-phosphate (compound of Example 3).

At a curing rate of 20 m/min, the printing ink is fast to wiping and resistant to 48 MEK double-rub tests.

Comparison with compound B

A flexo printing ink is prepared and tested analogously to Example 24, but the photoinitiator of Example 1 according to the invention is replaced by di(4-tert-butylphenyl) iodonium hexafluorophosphate (B).

Even at a reduced curing rate of 5 m/min, the printing ink is still not fast to wiping and does not withstand a single MEK double-rub test.

Comparison with compound C

A flexo printing ink is prepared and tested analogously to Example 24, but the photoinitiator of Example 1 according to the invention is replaced by di(4-isobutylphenyl) iodonium hexafluorophosphate (C).

The printing ink is not fast to wiping until a curing rate of 20 m/min and it is resistant to 9 MEK double-rub test.

Comparison with compound E

A flexo printing ink is prepared and tested analogously to Example 24, but the photoinitiator of Example 1 according to the invention is replaced by n-decylphenyl-phenyliodonium hexafluorophosphate (E).

The printing ink is not fast to wiping until a curing rate of 30 m/min and it is resistant to 2 MEK double-rub tests.

EXAMPLE 28

Positive Photoresist

A composition is prepared by dissolving 37.5 parts of poly[(4-tetrahydropyranyloxystyrene)-co-(4-hydroxystyrene)] with a 31 mol % proportion of 4-tetrahydropyranyloxystyrene and a 69 mol % proportion of 4-hydroxystyrene in 120 parts of propylene glycol methyl ether acetate (PGMEA) and subsequently dissolving one of the iodonium salts mentioned below, in each case in a concentration of 2.0%, based on the amount of polymer present, and is applied, analogously to Example 17, in a layer thickness of 1 micrometer, to an aluminium sheet by spin-coating at 2000 revolutions per minute. After 60 seconds' drying on a heating plate at 110° C., analogously to Example 17 exposure is effected through a multidensity chrome mask using the contact process with a high-pressure mercury lamp and a penetrative UV exposure apparatus Oriel Type 7800 for 120 seconds. The intensity of radiation, measured using an OAI 220 measuring probe, is 1.4 mW/cm$^2$ and using an OAI 400 measuring probe is 2.3 mW/cm$^2$. Before development, a post-exposure bake is effected at 100° C. on a heating plate for a duration of 60 seconds. The layer is developed for 60 seconds in aqueous 2.38% tetramethylammonium hydroxide solution, rinsed in water for 10 seconds and blown dry with compressed air.

Determination of the minimum relative exposure dose is carried out as described in Example 17, but in this case the first transmission field at which the positive resist was completely removed in the developer was determined.

The following results were obtained:

a) (4-isobutylphenyl)-p-tolyl-iodonium hexafluorophosphate, compound of Example 1, as iodonium salt:
The minimum transmission value at which the resist is fully developed is 16%, corresponding to an exposure energy of 26.9 mJ/cm$^2$ using an OAI 220 probe.

b) (4-isobutylphenyl)-m-tolyl-iodonium hexafluorophosphate, compound of Example 6, as iodonium salt:
The minimum transmission value at which the resist is fully developed is also 16%, corresponding to an exposure energy of 26.9 mJ/cm$^2$ using an OAI 220 probe.

c) (4-isobutylphenyl)-p-tolyl-iodonium p-tosylate, compound of Example 11, as iodonium salt:
The minimum transmission value at which the resist is fully developed is also 16%, corresponding to an exposure energy of 26.9 mJ/cm$^2$ using an OAI 220 probe.

EXAMPLE 29

Chemically Amplified Positive Photoresist

A chemically amplified positive resist formulation is prepared by mixing the following components:

100.00 parts of a resin binder (a copolymer of 22 mol-% of styrene, 69 mol-% of p-hydroxystyrene and 9 mol-% of t-butyl acrylate, having a Mw of 9850; $^{RTM}$Maruzen MARUKA LYNCUR PHS/STY/TBA, provided by Maruzen Oil Company, Japan)

0.48 parts of a levelling agent (FC-430, provided by 3M)

475.00 parts of propylene glycol methyl ether acetate (PGMEA) (provided by Tokyo Kasei, Japan)

4.0 parts of the photoacid generator of example 14

The resist formulation is spin coated onto a hexamethyl dimethylsilane-treated silicone wafer at 3000 rpm for 45 seconds and softbaked for 90 seconds at 140° C. on a hotplate to obtain a film thickness of 800 nm. The resist film is then exposed to deep UV radiation of 254 nm wavelength through a narrow band interference filter and a multidensity quartz mask using an Ushio's high pressure mercury lamp, UXM-501 MD, and a mask aligner Canon PLA-521. The samples then are post exposure baked for 90 seconds at 1 40° C. on a hotplate and developed. The exposure intensity is measured with a Unimeter UIT-150 from Ushio. The Dose to Clear (E$_0$), which is the dose just sufficient to completely remove the resist film with 60 seconds immersion development in 1.79% aqueous tetramethyl ammonium hydroxide developer is determined from the measured contrast curve. The Dose to Clear (E$_0$) is 0.68 mJ/cm$^2$.

What is claimed is:

1. A radiation-sensitive composition comprising (a1) a cationically or acid-catalytically polymerisable or crosslinkable compound or (a2) a compound that increases its solubility in a developer under the action of acid; and (b) at least one diaryliodonium salt of formula I

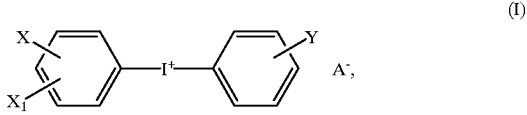

X is branched $C_3$–$C_{20}$alkyl or $C_3$–$C_8$cycloalkyl;

$X_1$ is hydrogen, linear $C_1$–$C_{20}$alkyl, branched $C_3$–$C_{20}$alkyl or $C_3$–$C_8$cycloalkyl;

with the proviso that the sum of the carbon atoms in X and $X_1$ is at least 4;

Y is linear $C_1$–$C_{10}$alkyl, branched $C_3$–$C_{10}$alkyl or $C_3$–$C_8$cycloalkyl;

A$^-$ is a non-nucleophilic anion, selected from the group $(BF_4)^-$, $(SbF_6)^-$, $(PF_6)^-$, $(B(C_6F_5))_4^-$, $C_1$–$C_{20}$alkylsulfonate, $C_2$–$C_{20}$haloalkylsulfonate, unsubstituted $C_6$–$C_{10}$arylsulfonate, camphorsulfonate, $C_1$–$C_{20}$-perfluoroalkylsulfonylmethide, $C_1$–$C_{20}$-perfluoroalkylsulfonylimide, and $C_6$–$C_{10}$arylsulfonate substituted by halogen, $NO_2$, $C_1$–$C_{12}$alkyl, $C_1$–$C_{12}$halo-alkyl, $C_1$–$C_{12}$alkoxy or by COOR$_1$; and R$_1$ is $C_1$–$C_{20}$alkyl, phenyl, benzyl; or phenyl mono- or poly-substituted by $C_1$–$C_{12}$alkyl, $C_1$–$C_{12}$alkoxy or by halogen;

with the proviso that the two phenyl rings on the iodine atom are not identically substituted.

2. A radiation-sensitive composition according to claim 1, wherein in the compounds of formula I X is branched $C_4$–$C_{12}$alkyl or cyclohexyl.

3. A radiation-sensitive composition according to claim 1, wherein in the compounds of formula I Y is linear $C_1$–$C_6$alkyl or cyclohexyl.

4. A radiation-sensitive composition according to claim 1, wherein in the compounds of formula I A$^-$ is a non-nucleophilic anion, selected from the group $(PF_6)^-$, $(B(C_6F_5))_4^-$, $C_1$–$C_{12}$-alkylsulfonate, $C_2$–$C_{12}$haloalkylsulfonate, unsubstituted phenylsulfonate, camphorsulfonate, $C_1$–$C_{20}$-perfluoroalkylsulfonylmethide, $C_1$–$C_{20}$-perfluoroalkylsulfonylimide, and phenylsulfonate substituted by halogen, $NO_2$, $C_1$–$C_{12}$alkyl, $C_1$–$C_{12}$haloalkyl, $C_1$–$C_{12}$-alkoxy or by COOR$_1$.

5. A radiation-sensitive composition according to claim 1, wherein in the compounds of formula I X is branched $C_4$–$C_6$alkyl or cyclohexyl;

$X_1$ is hydrogen or branched $C_4$–$C_6$alkyl;

Y is linear $C_1$–$C_4$alkyl, branched $C_3$–$C_4$alkyl or cyclohexyl;

A$^-$ is a non-nucleophilic anion, selected from the group (PF$_6$)$^-$, camphorsulfonate and $C_1$–$C_4$alkyl-substituted phenylsulfonate.

6. A radiation-sensitive composition according to claim 1, wherein component (a1) is at least one compound selected from the group of cycloaliphatic epoxy compounds, glycidyl ethers, oxetane compounds, vinyl ethers, acid-crosslinkable melamine resins, acid-crosslinkable hydroxymethylene compounds and acid-crosslinkable alkoxymethylene compounds.

7. A radiation-sensitive composition according to claim 1, wherein component (a2) is at least one compound selected from the group of cycloaliphatic copolymers, 4-hydroxyphenyl-group-containing copolymers, maleic acid anhydride-containing copolymers and acrylic acid-, acrylic acid ester- and methacrylic acid ester-containing copolymers, with the proviso that those copolymers carry functional groups that increase the solubility of the polymer in an alkaline developer after reaction with an acid.

8. A radiation-sensitive composition according to claim 1, additionally to components (a1) or (a2) and (b) comprising at least one sensitizer compound (d).

9. A radiation-sensitive composition according to claim 8, wherein the sensitizer compound (d) is benzophenone, thioxanthone, anthracene or derivatives thereof.

10. A method for the photopolymerisation or crosslinking of cationically or acid-catalytically polymerisable or crosslinkable compounds under the action of electromagnetic radiation or an electron beam, in which method a compound of formula I according to claim 1 is used as photolatent acid donor.

11. A coated substrate that is coated on at least one surface with a composition according to claim 1.

12. A method for the production of relief images, wherein a composition according to claim 1 is applied to a substrate and is then exposed image-wise.

13. A photoresist comprising a compound of formula I according to claim 1 as radiation-sensitive acid donor.

14. A photoresist according to claim 13, wherein the photoresist is a negative resist.

15. A photoresist according to claim 13, wherein the photoresist is a positive resist.

16. A photoresist according to claim 13, wherein the photoresist is a chemically enhanced resist.

17. Method according to claim 10 in the manufacture of surface-coating compositions, powder coating compositions, printing inks, printing plates, dental compounds, stereolithography resins, adhesives, anti-adhesive coatings, color filters, resist materials or image-recording materials.

18. A compound of formula I according to claim 1.

* * * * *